(12) United States Patent
Lee et al.

(10) Patent No.: US 12,364,776 B2
(45) Date of Patent: Jul. 22, 2025

(54) GANGLIOGLIOMA-INDUCED ANIMAL MODEL AND A METHOD FOR DIAGNOSING AND TREATING GANGLIOGLIOMA AND RELATED DISEASES

(71) Applicants: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

(72) Inventors: Jeong Ho Lee, Daejeon (KR); Hyun Yong Koh, Daejeon (KR); Dong Seok Kim, Seoul (KR)

(73) Assignees: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

( * ) Notice: Subject to any disclaimer, the term of this patent is extended or adjusted under 35 U.S.C. 154(b) by 955 days.

(21) Appl. No.: 16/486,905

(22) PCT Filed: Jun. 26, 2018

(86) PCT No.: PCT/KR2018/007234
§ 371 (c)(1),
(2) Date: Aug. 19, 2019

(87) PCT Pub. No.: WO2019/004703
PCT Pub. Date: Jan. 3, 2019

(65) Prior Publication Data
US 2020/0360537 A1   Nov. 19, 2020

(30) Foreign Application Priority Data

Jun. 29, 2017  (KR) .................. 10-2017-0082630
Jun. 29, 2017  (KR) .................. 10-2017-0082631
Jun. 29, 2017  (KR) .................. 10-2017-0082632

(51) Int. Cl.
| | |
|---|---|
| *A61K 49/00* | (2006.01) |
| *A01K 67/0275* | (2024.01) |
| *A61K 31/437* | (2006.01) |
| *A61K 31/506* | (2006.01) |
| *C12Q 1/6883* | (2018.01) |
| *C12Q 1/6886* | (2018.01) |

(52) U.S. Cl.
CPC ...... *A61K 49/0008* (2013.01); *A01K 67/0275* (2013.01); *A61K 31/437* (2013.01); *A61K 31/506* (2013.01); *C12Q 1/6883* (2013.01); *C12Q 1/6886* (2013.01); *A01K 2217/206* (2013.01); *A01K 2227/105* (2013.01); *A01K 2267/0331* (2013.01); *C12Q 2600/156* (2013.01)

(58) Field of Classification Search
CPC ........ A01K 2217/206; A01K 2227/105; C12N 9/12
See application file for complete search history.

(56) References Cited

U.S. PATENT DOCUMENTS

2014/0378324 A1* 12/2014 Lavoie ............... C12N 9/12
435/7.6

FOREIGN PATENT DOCUMENTS

| JP | 2013-543117 | 11/2013 |
|---|---|---|
| KR | 10-2012-0099630 | 9/2012 |
| KR | 10-2015-0142932 | 12/2015 |

OTHER PUBLICATIONS

Mercer, K. et al. Expression of endogenous oncogenic V600EB-raf induces proliferation and developmental defects in mice and transformation of primary fibroblasts. Cancer Res. 65, 11493-11500. (Year: 2005).*
Galabova-Kovacs, Gergana, et al. "Essential role of B-Raf in oligodendrocyte maturation and myelination during postnatal central nervous system development." The Journal of cell biology 180, No. 5: 947-955. (Year: 2008).*
Wefers, Benedikt. The role of ERK/MAPK signalling in emotional behaviour-studies on Braf knockout and gain-of-function mutant mice. Diss. Technische Universität München. (Year: 2011).*
Mercer, K. et al. Expression of endogenous oncogenic V600EB-raf induces proliferation and developmental defects in mice and transformation of primary fibroblasts. Cancer Res. 65, 11493-11500 (2005). (Year: 2005).*
Galabova-Kovacs, et al Essential role of B-Raf in oligodendrocyte maturation and myelination during postnatal central nervous system development. The Journal of cell biology 180, No. 5 (2008): 947-955. (Year: 2008).*
Wefers, B. (2011). The role of ERK/MAPK signalling in emotional behaviour-studies on Braf knockout and gain-of-function mutant mice (Doctoral dissertation, Technische Universität München). (Year: 2011).*
Simeonova, I., Huillard, E. In vivo models of brain tumors: roles of genetically engineered mouse models in understanding tumor biology and use in preclinical studies. Cell. Mol. Life Sci. 71, 4007-4026 (Year: 2014).*

(Continued)

*Primary Examiner* — J. E. Angell
*Assistant Examiner* — Josephine M Gonzales
(74) *Attorney, Agent, or Firm* — LEX IP MEISTER, PLLC

(57) ABSTRACT

The present invention relates to a biomarker of epilepsy, a composition for diagnosing epilepsy, an epilepsy-induced animal, and a composition for preventing or treating epilepsy, and specifically, relates to a composition for diagnosing epilepsy comprising a BRAF mutant protein and a nucleic acid molecule, and an agent capable of detecting the protein or nucleic acid molecule, an epilepsy-induced animal transformed with the BRAF mutant nucleic acid molecule, and a composition for prevention or treatment of epilepsy comprising a BRAF mutant protein activity inhibitor.

5 Claims, 19 Drawing Sheets

Specification includes a Sequence Listing.

(56) References Cited

OTHER PUBLICATIONS

Martinoni et al. (Journal of Clinical Neuroscience, 2015; filed on Mar. 29, 2021 (Year: 2015).*

Huillard, Emmanuelle, et al. "Cooperative interactions of BRAFV600E kinase and CDKN2A locus deficiency in pediatric malignant astrocytoma as a basis for rational therapy." Proceedings of the National Academy of Sciences 109.22: 8710-8715. (Year: 2012).*

Kanemaru, Yu, et al. "Dramatic response of BRAF V600E-mutant epithelioid glioblastoma to combination therapy with BRAF and MEK inhibitor: establishment and xenograft of a cell line to predict clinical efficacy." Acta Neuropathologica Communications 7: 1-11. (Year: 2019).*

Martinoni, M et al., "BRAF V600E mutation in neocortical posterior temporal epileptogenic gangliogliomas", Journal of Clinical Neuroscience vol. 22, pp. 1250-1253, 2015.

Bufalo, F. et al., "Response of recurrent BRAFV600E mutated ganglioglioma to Vemurafenib as single agent", Journal of Translational Medicine, vol. 12, pp. 1-7, 2014.

H. Neurath et al., , "The Proteins", 3rd Edition, vol. 4, Academic Press, New York, 1979.

Schindler G et al., "Analysis of Braf V600E mutation in 1,320 nervous system tumors reveals high mutation frequencies in pleomorphic xanthoastrocytoma, ganglioglioma and extra-cerebellar pilocytic astrocytoma", Acta neuropathologica. 2011; 121(3):397-405.

Jelena Urosevic et al., "Constitutive activation of B-Raf in the mouse germ line provides a model for human cardio-facio-cutaneous syndrome", Proc. Natl. Acad. Sci. USA, 2011, 108(12):5015-5020, Supporting Information, Mar. 22, 2011.

Christian Koelsche et al., "Mutant Braf V600E protein in ganglioglioma is predominantly expressed by neuronal tumor cells", Acta Neuropathologica, 2013, 125(6):891-900, Feb. 24, 2013.

Genevieve Schindler et al., "Analysis of Braf V600E mutation in 1,320 nervous system tumors reveals high mutation frequencies in pleomorphic xanthoastrocytoma, ganglioglioma and extra-cerebellar pilocytic astrocytoma", Acta Neuropathologica, 2011, 121(3):397-405, Jan. 29, 2011.

Dolly Aguilera et al., "Successful Retreatment of a Child with a Refractory Brainstem Ganglioglioma with Vemurafenib", Pediatr. Blood Cancer, 2016, vol. 63, pp. 541-543, Nov. 18, 2015.

Canadian Journal of Neurological Sciences, 2016, vol. 43 Supplement S4, Abstracts: 17th Biennial Canadian Neuro-Oncology Meeting, p. S12, PS1-218, Jun. 9-11, 2016.

Neuronal tumor, [online], 2016, <URL: http://www.jsnp.jp/cerebral_5_main.htm> & its English translation of the related parts.

JP Robinson et al., "Activated BRAF induces gliomas in mice when combined with Ink4a/Arf loss or Akt activation", Oncogene, vol. 29, No. 3, Oct. 26, 2009, p. 335-344, XP055773549, Oct. 26, 2009.

An-Chi Tien et al., "Regulated temporal-spatial astrocyte precursor cell proliferation involves BRAF signalling in mammalian spinal cord", Development vol. 139, No. 14, p. 2477-2487, XP055774007, Jun. 6, 2012.

Quentin Breton et al., "BRAF-V600E immunohistochemistry in a large series of glial and glial-neuronal tumors" Brain and Behavior, vol. 7, No. 3, p. e00641, XP055773484, Feb. 10, 2017.

Francesca del Bufalo et al., "Response of recurrent BRAFV600E mutated ganglioglioma to Vemurafenib as single agent", Journal of Translational Medicine, Biomed Central, vol. 12, No. 1, p. 356, XP021207572, Dec. 19, 2014.

Matteo Martinoni et al., "BRAF V600E mutation in neocortical posterior temporal epileptogenic gangliogliomas", Journal of Clinical Neuroscience, vol. 22, No. 8, p. 1250-1253, XP055565822, Aug. 2015.

EPO, extended European Search Report of the corresponding European Patent Application No. 18822580.9., dated Mar. 12, 2021.

* cited by examiner

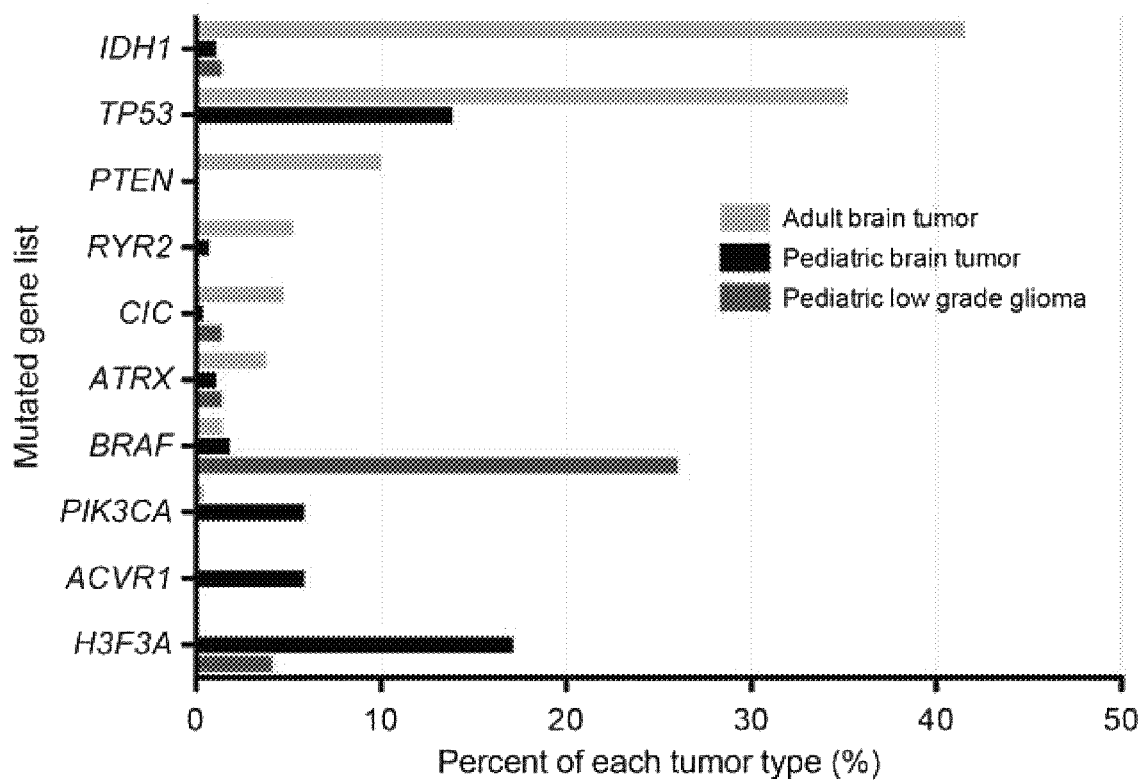
[FIG. 1a]

[FIG. 1b]
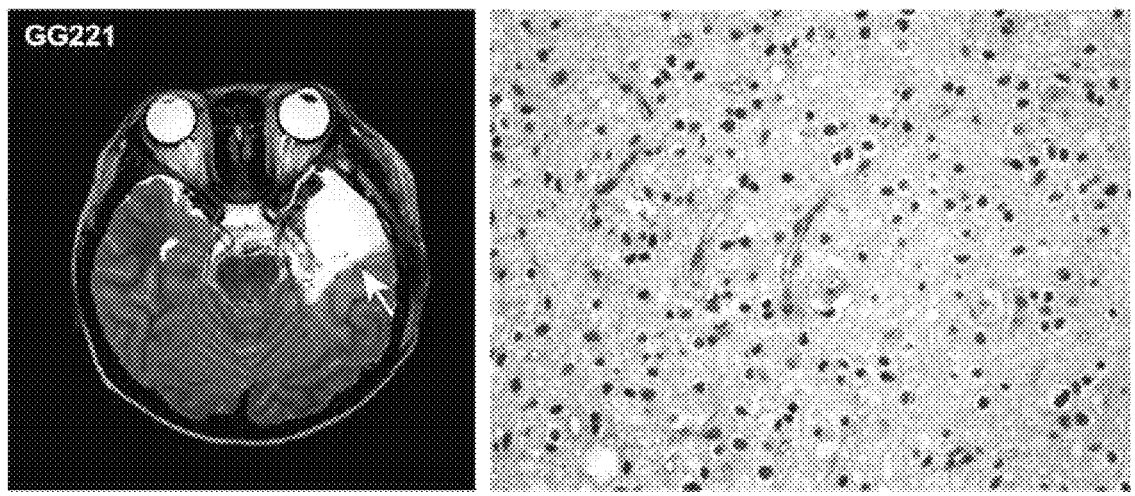
[FIG. 1c]
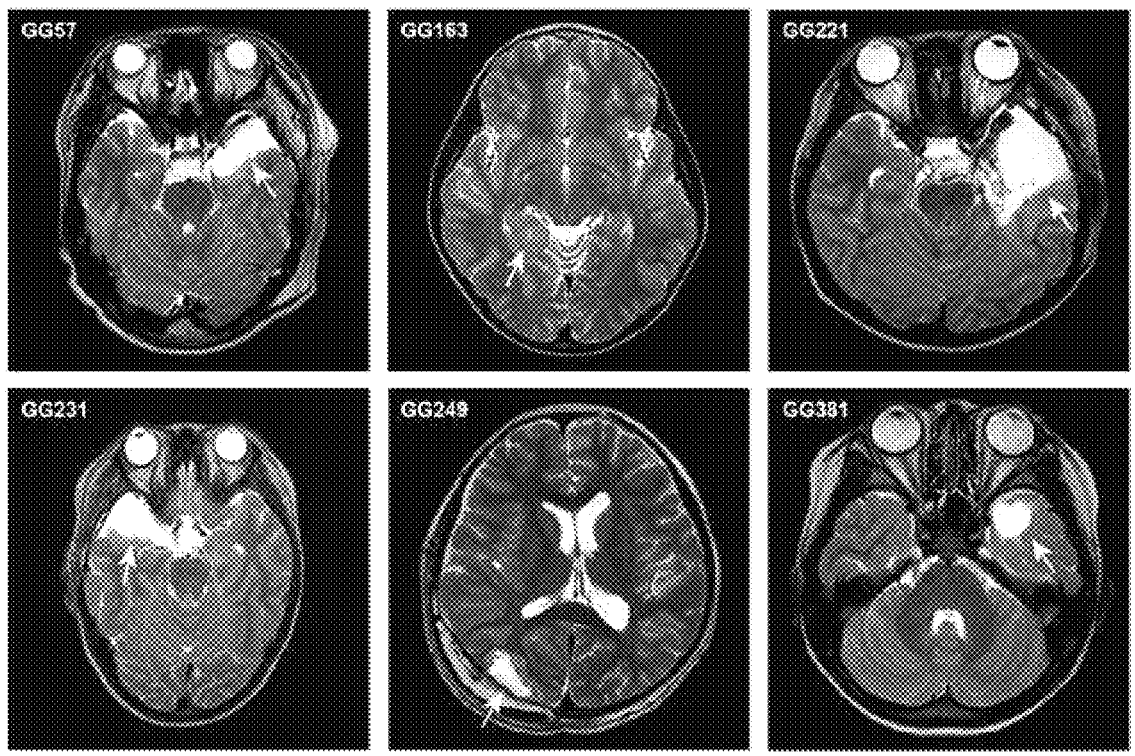

[FIG. 2a]
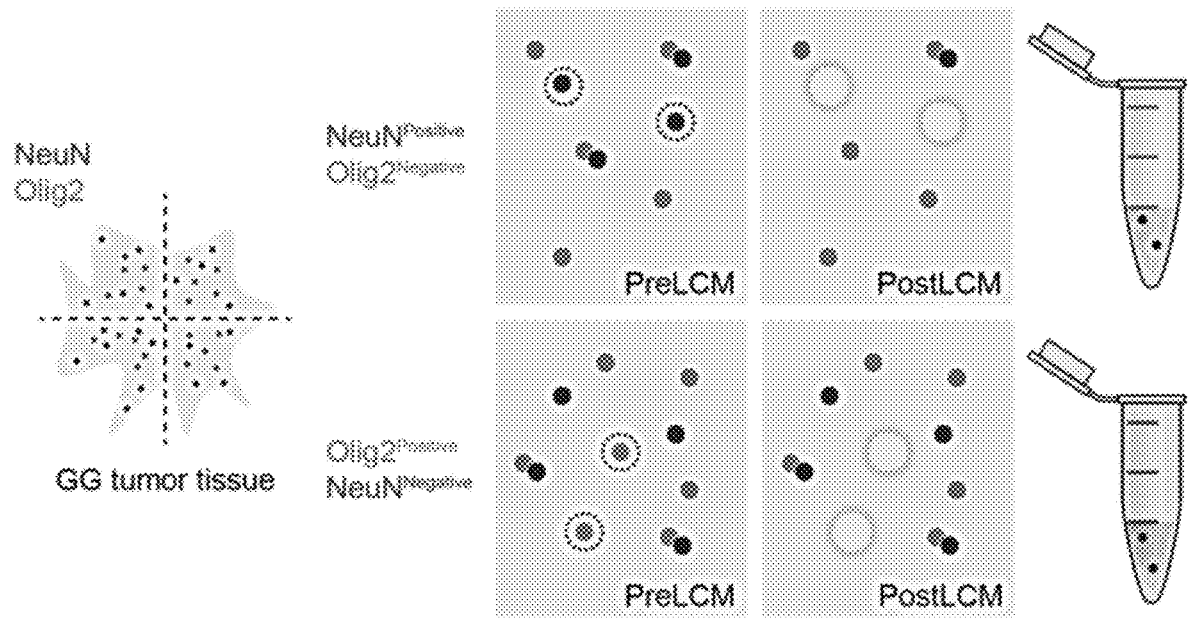
[FIG. 2b]
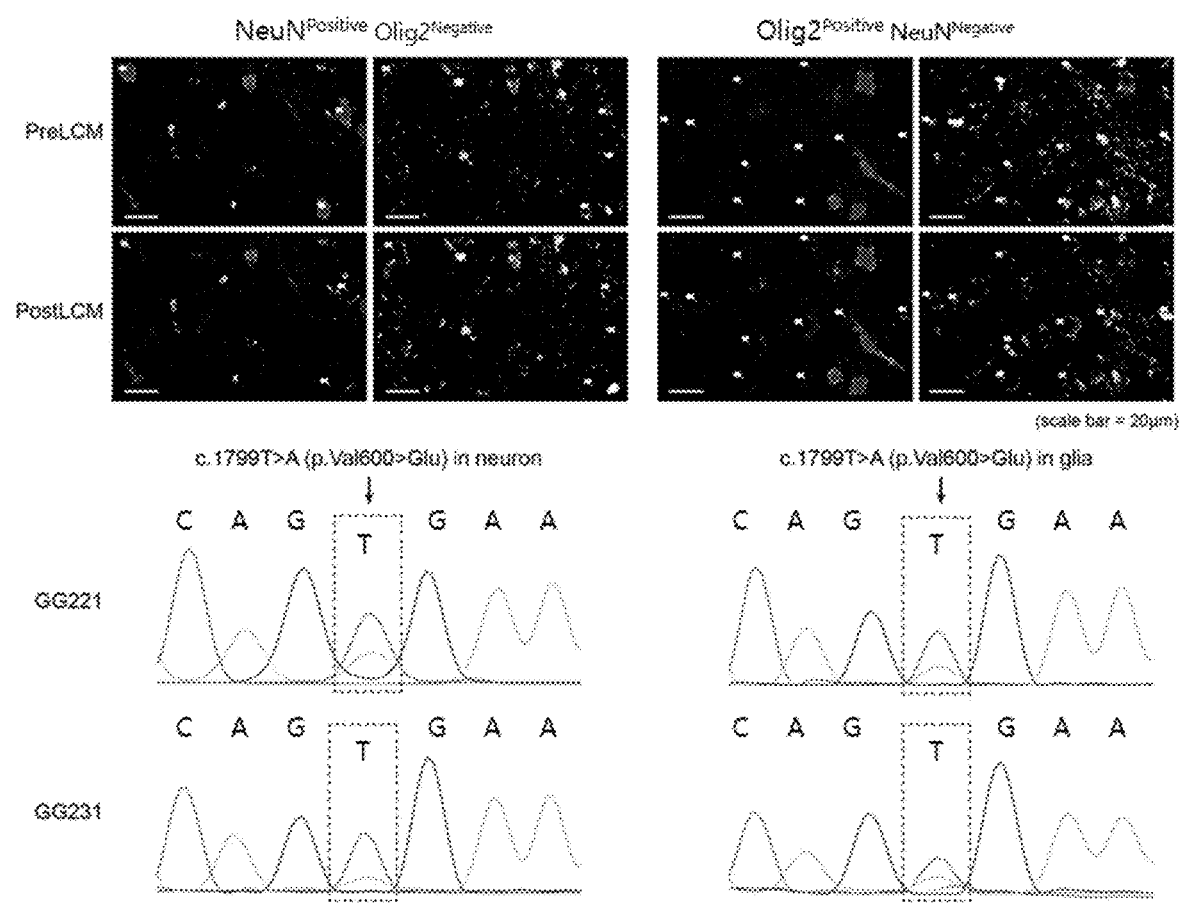

[FIG. 3a]
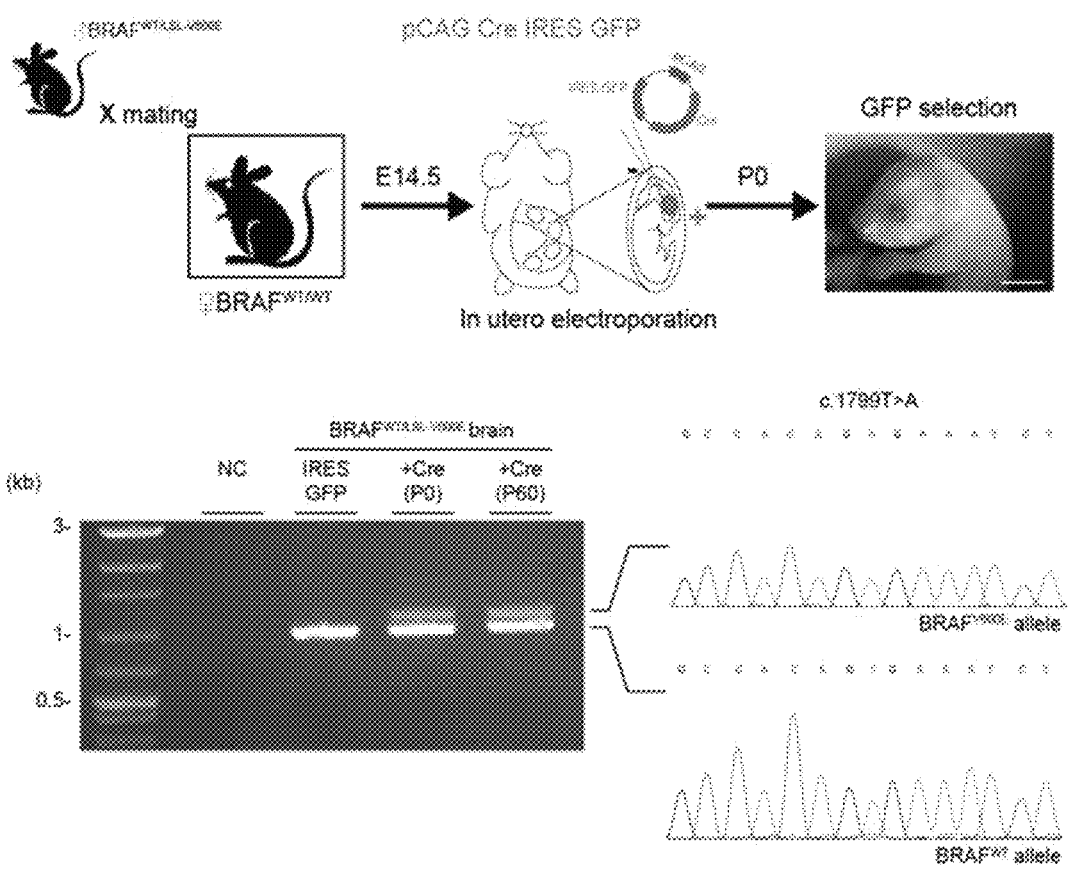

[FIG. 3b]
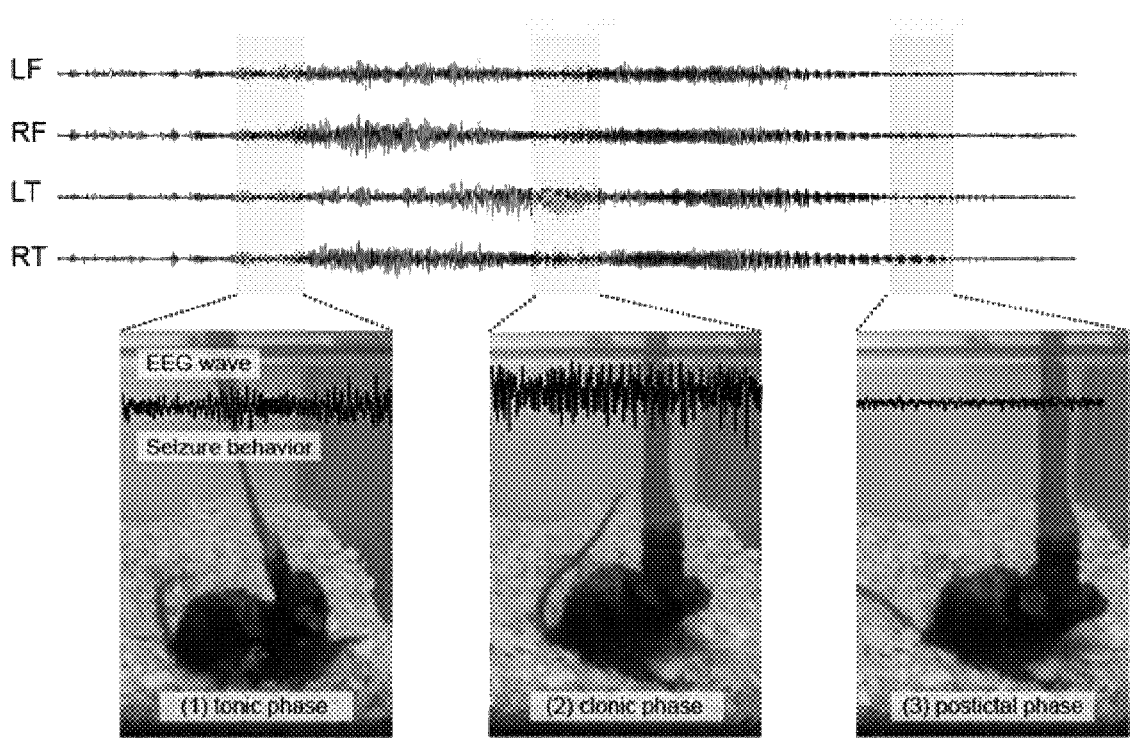

[FIG. 3c]
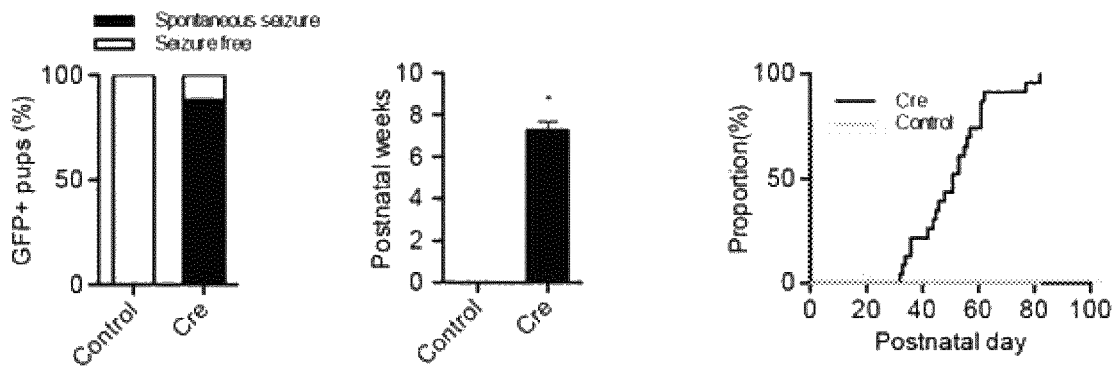
[FIG. 4]
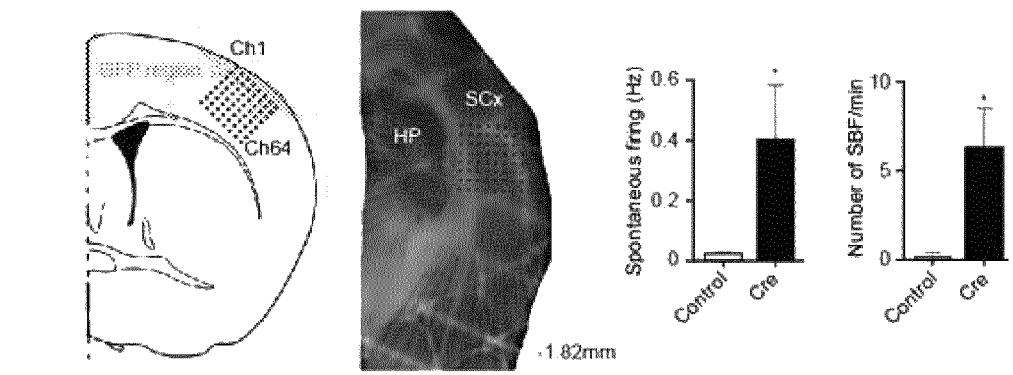
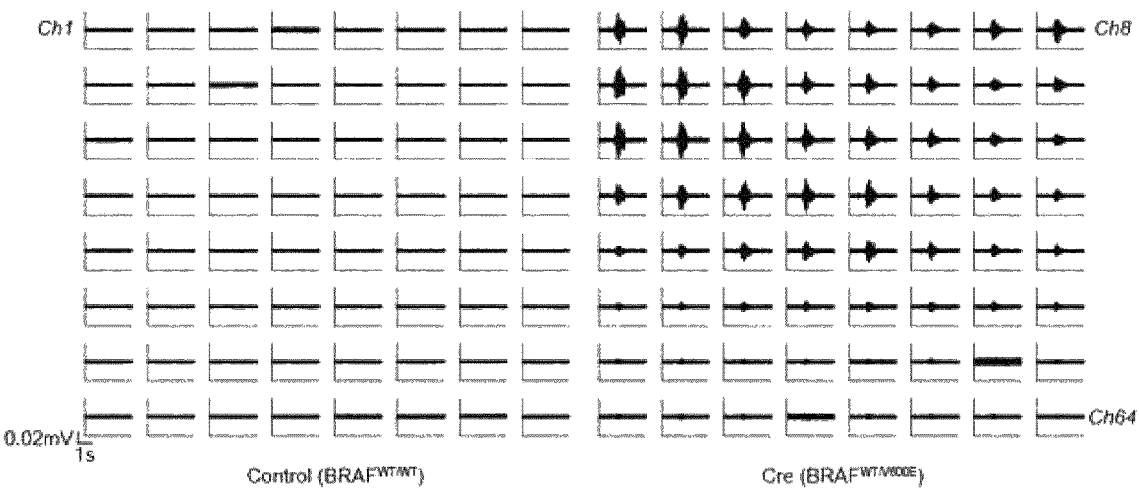

[FIG. 5]
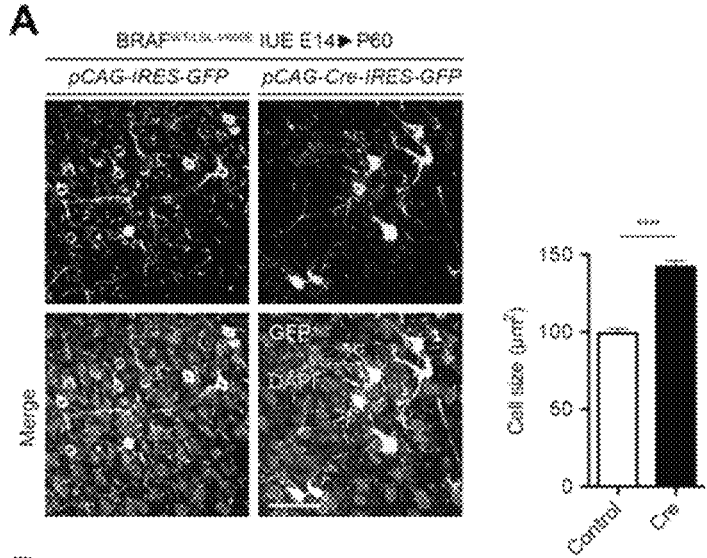
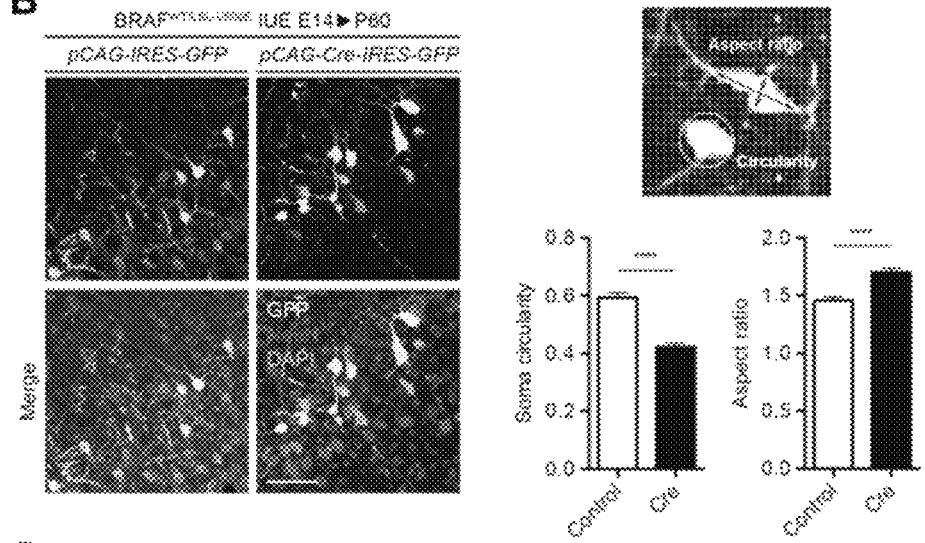
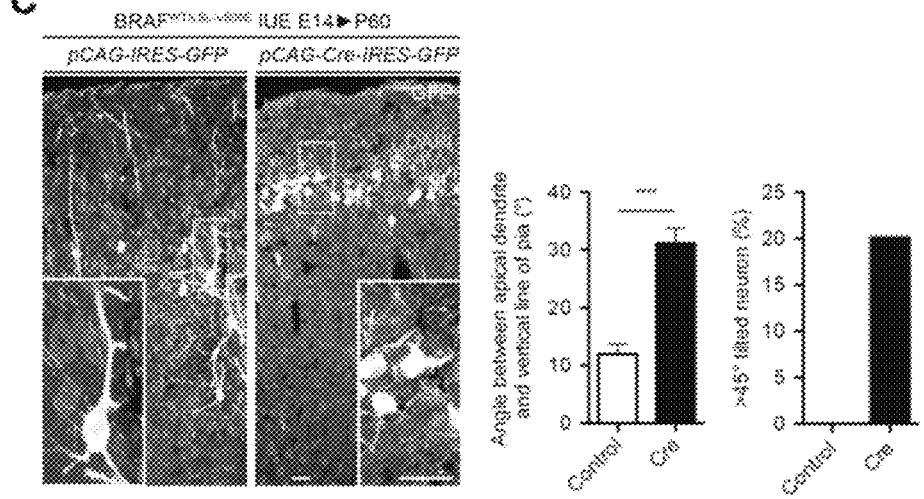

[FIG. 6a]
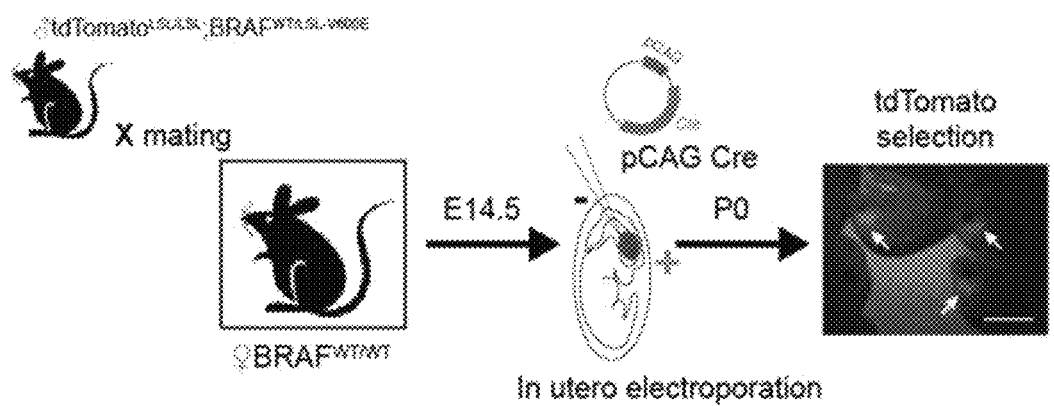
[FIG. 6b]
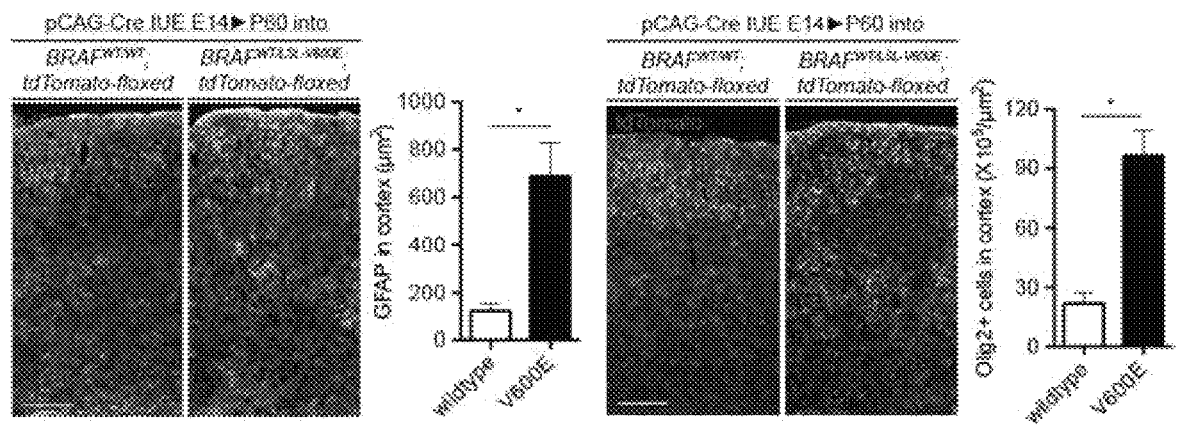

[FIG. 6c]
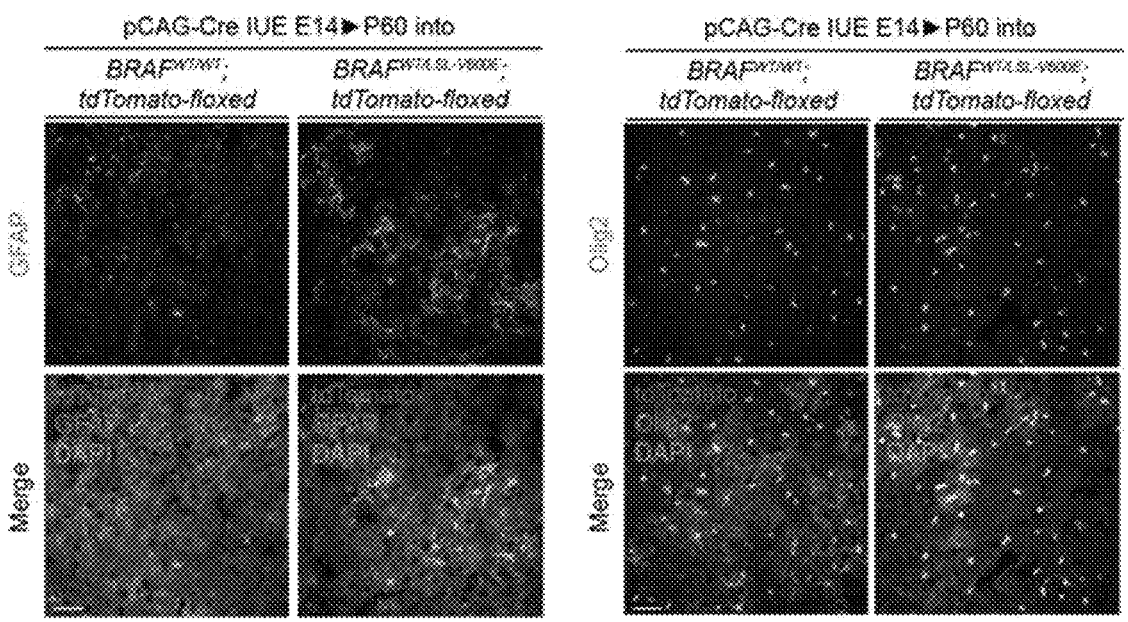
[FIG. 6d]
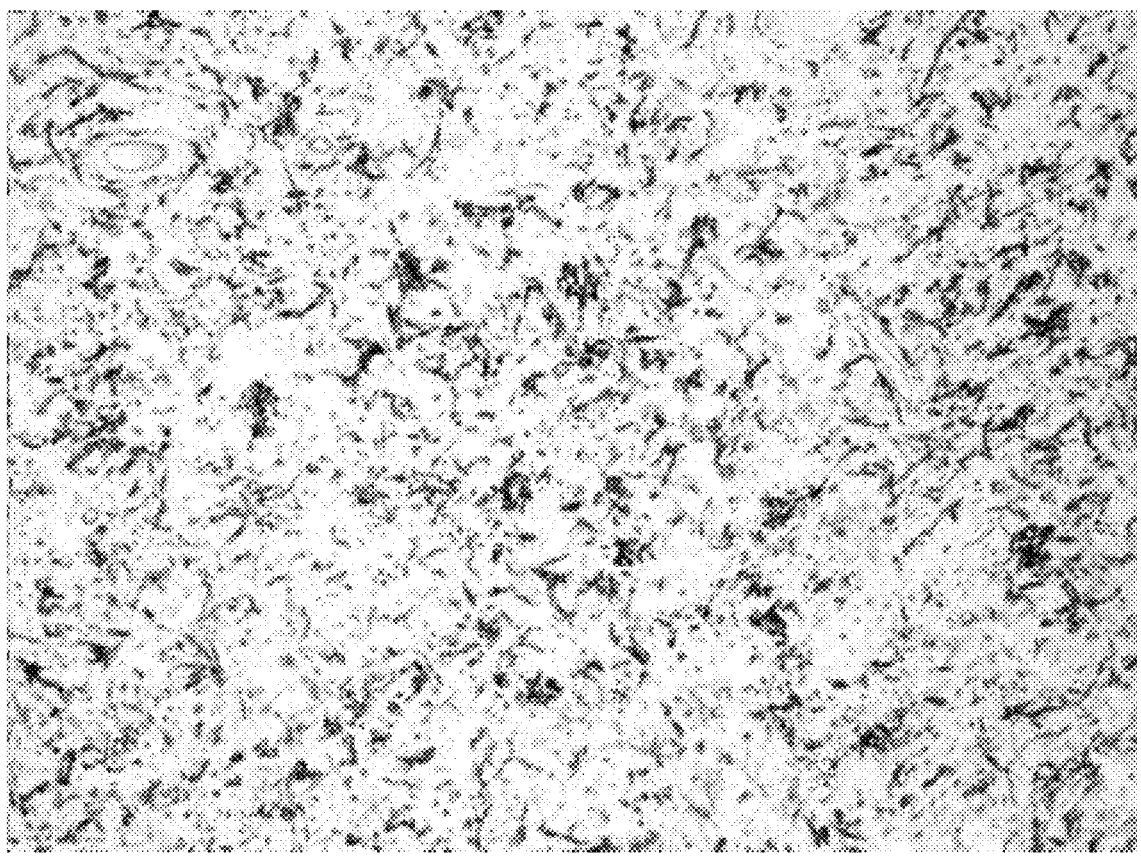

[FIG. 7]
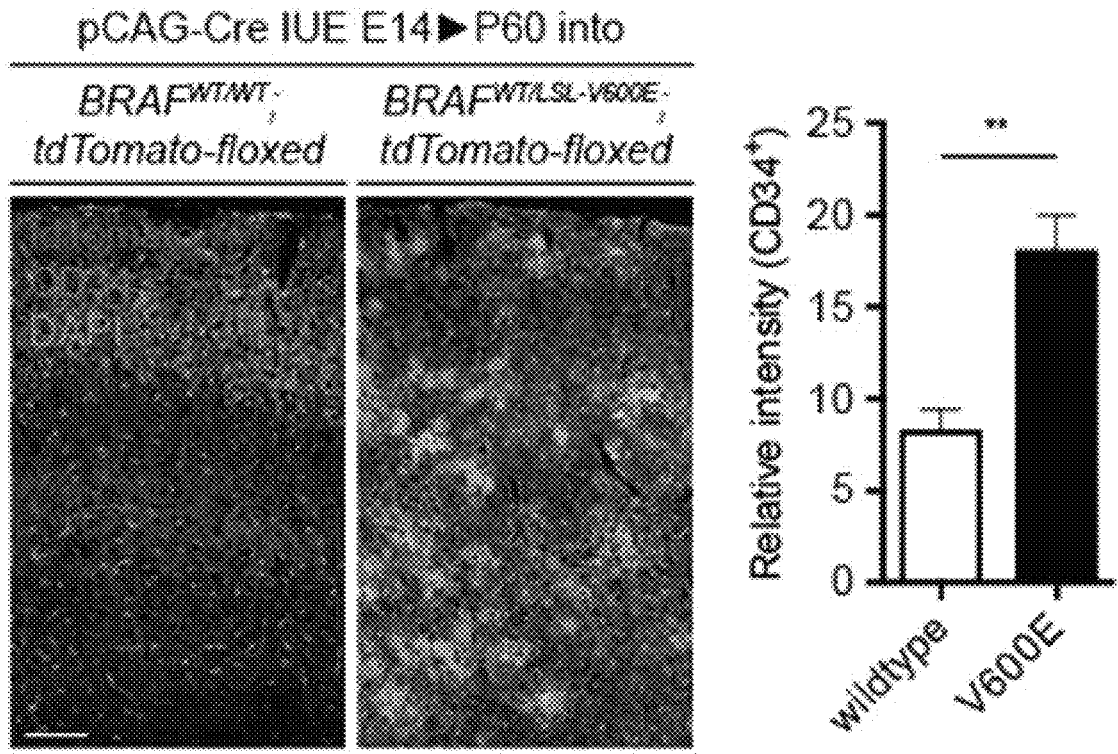
[FIG. 8]
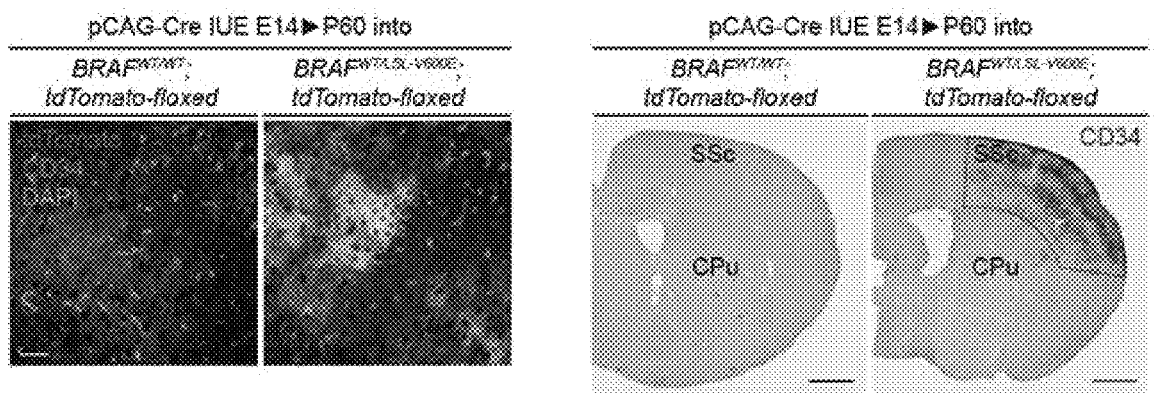

[FIG. 9]
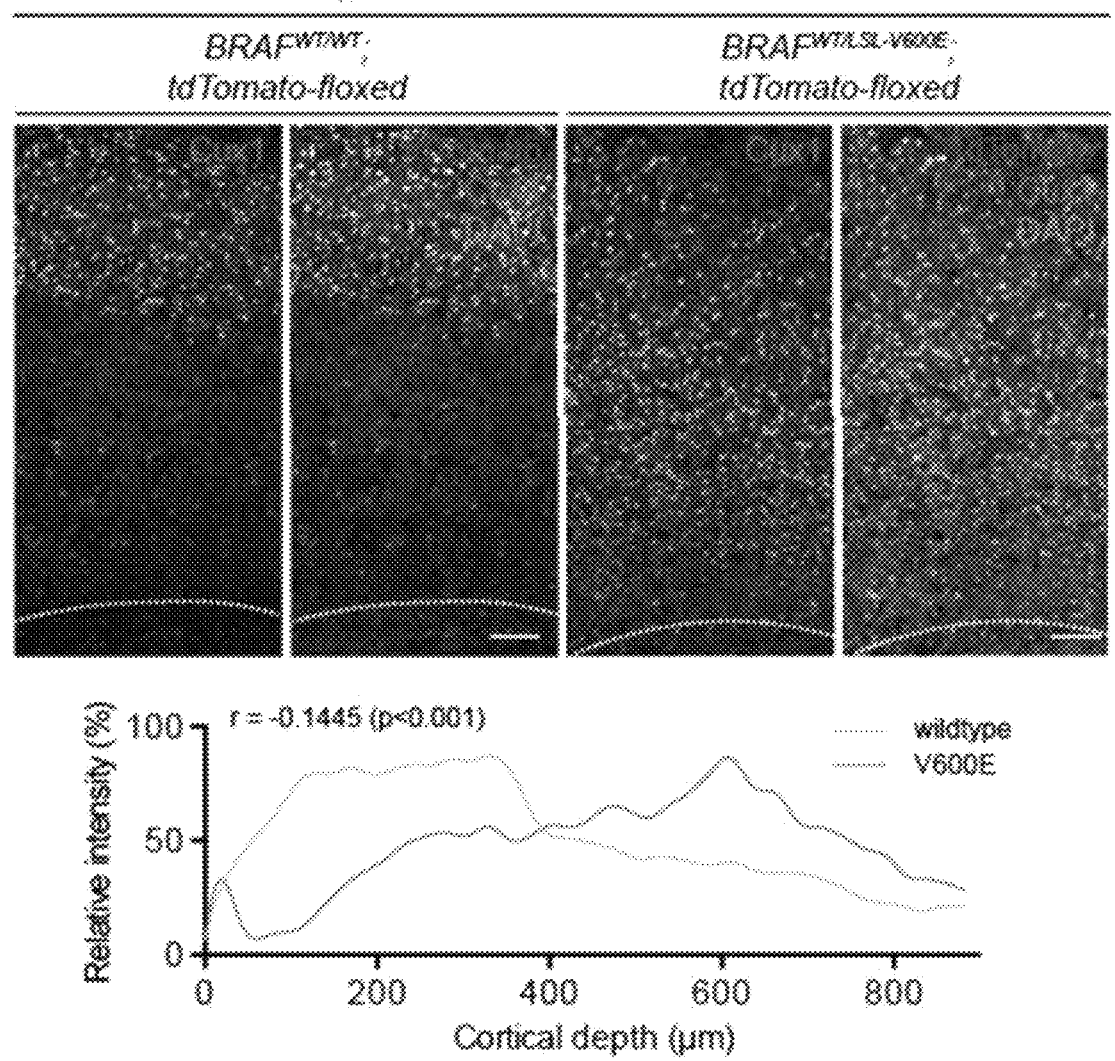

[FIG. 10]
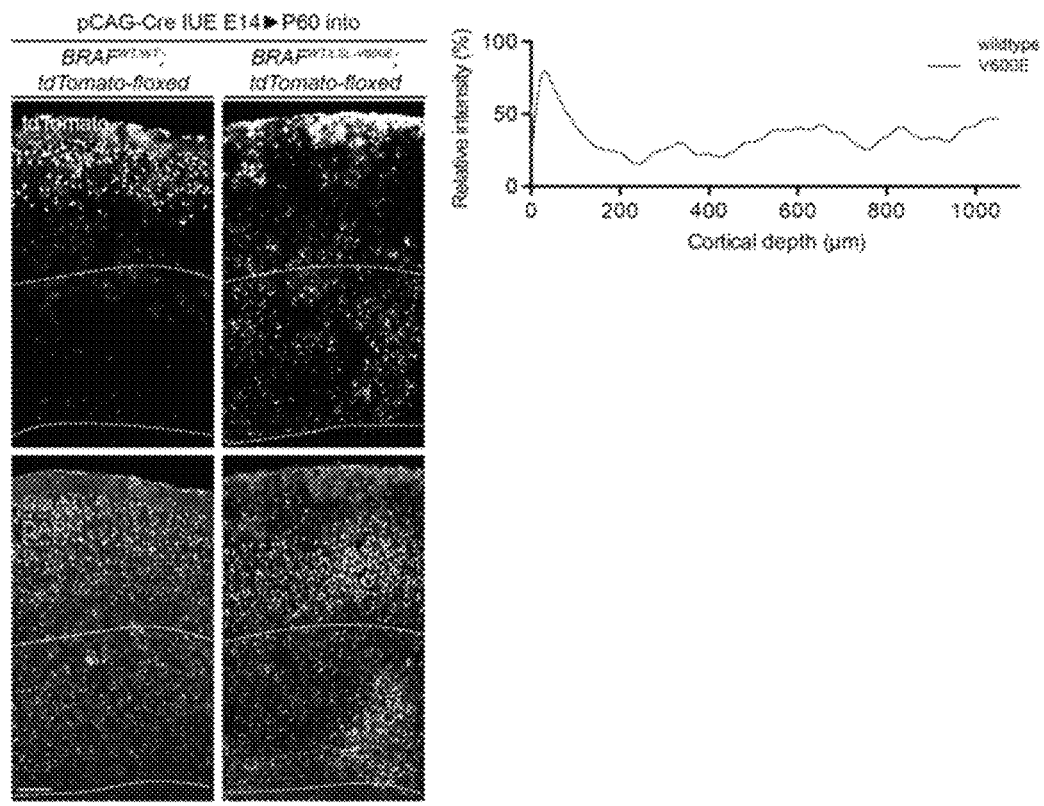
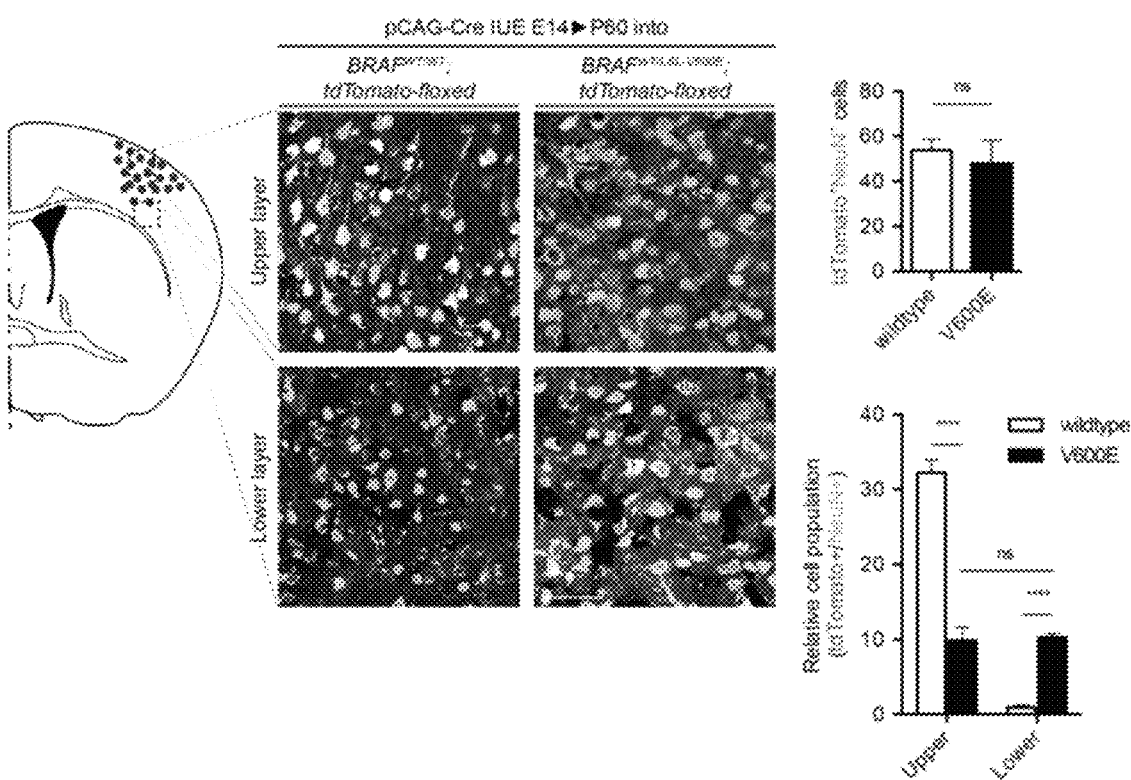

[FIG. 11]
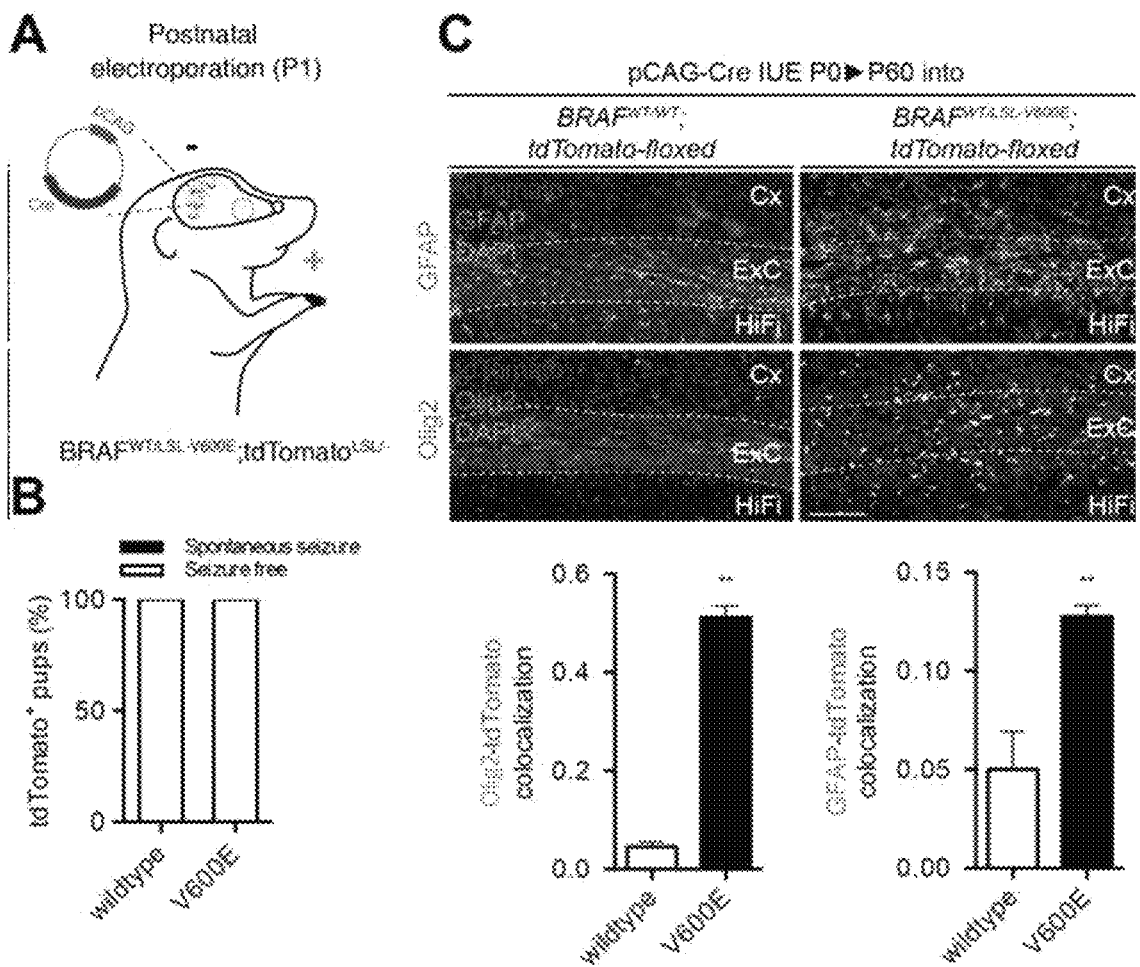

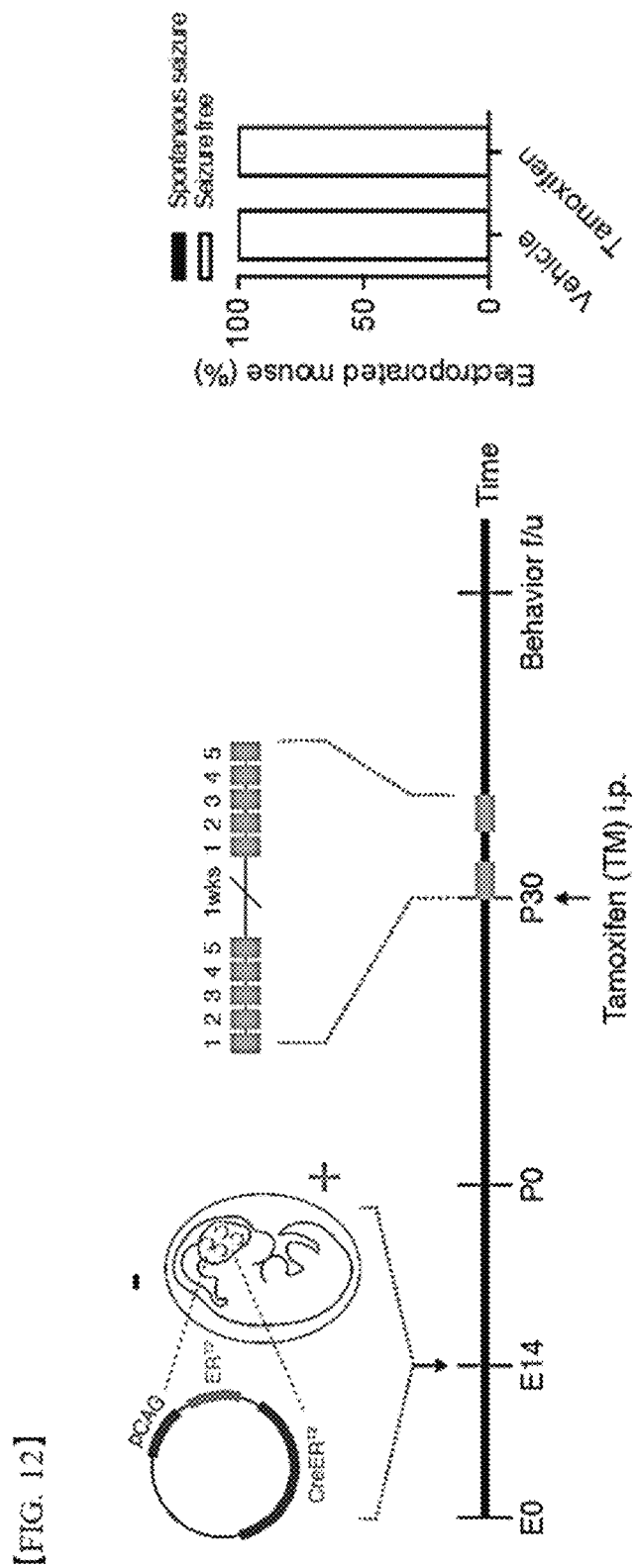
[FIG. 12]

[FIG. 13]
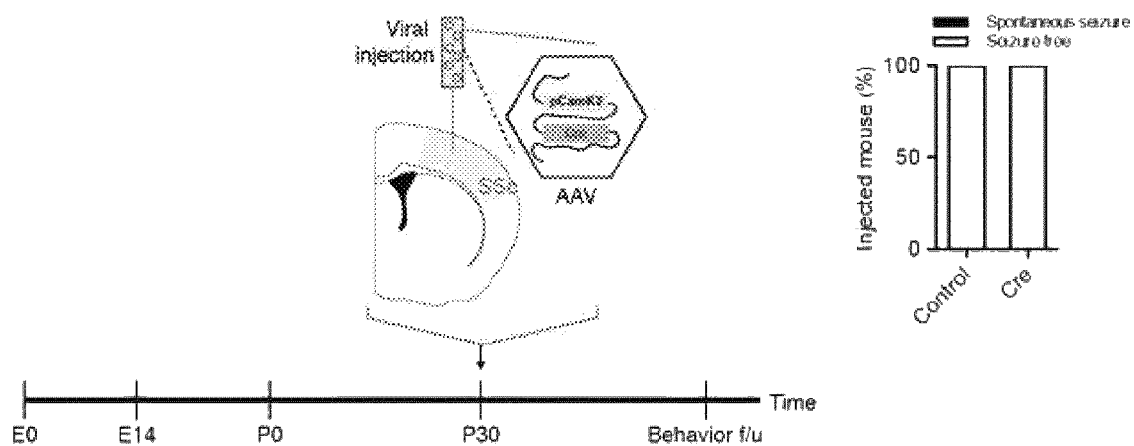

[FIG. 14]
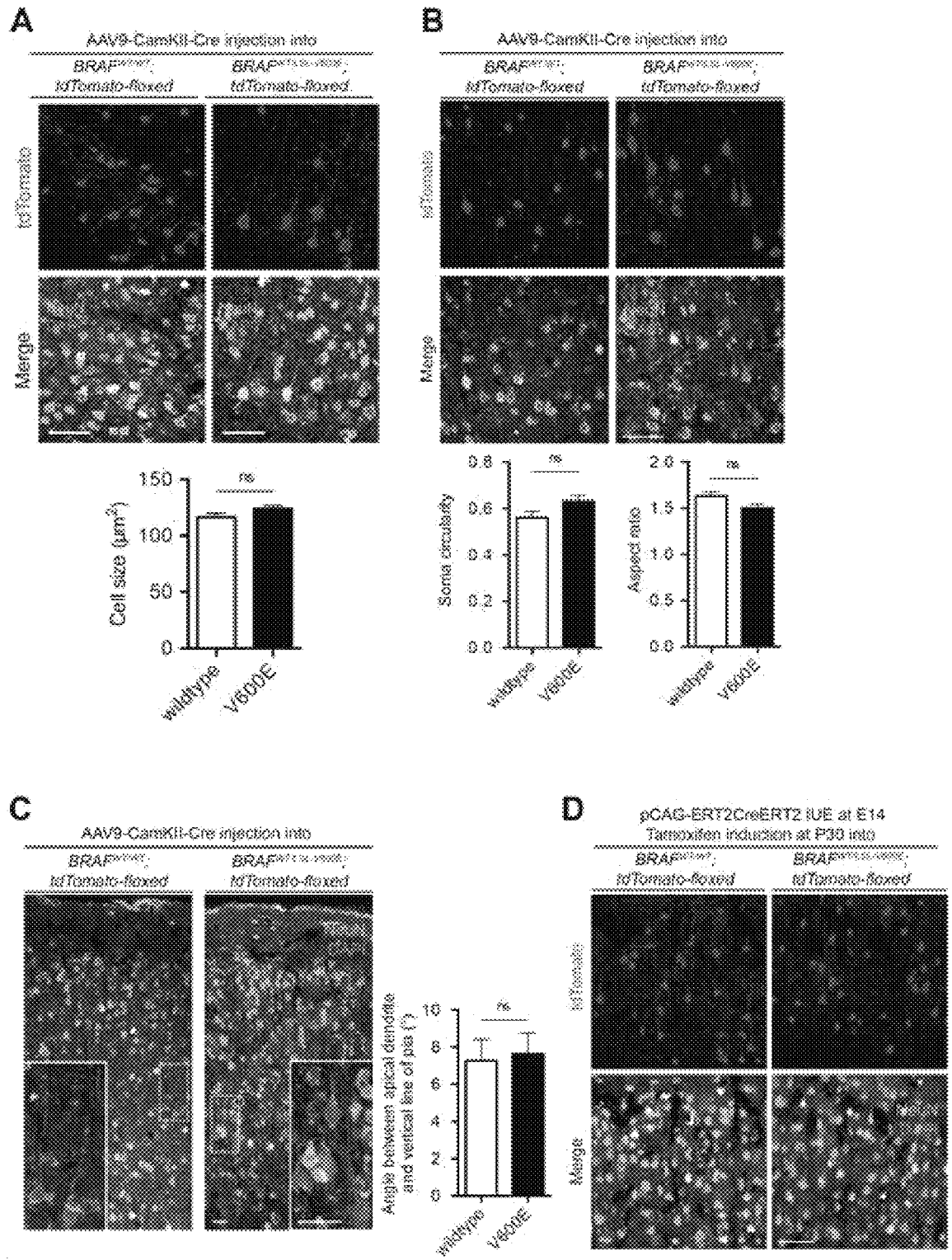

[FIG. 15]
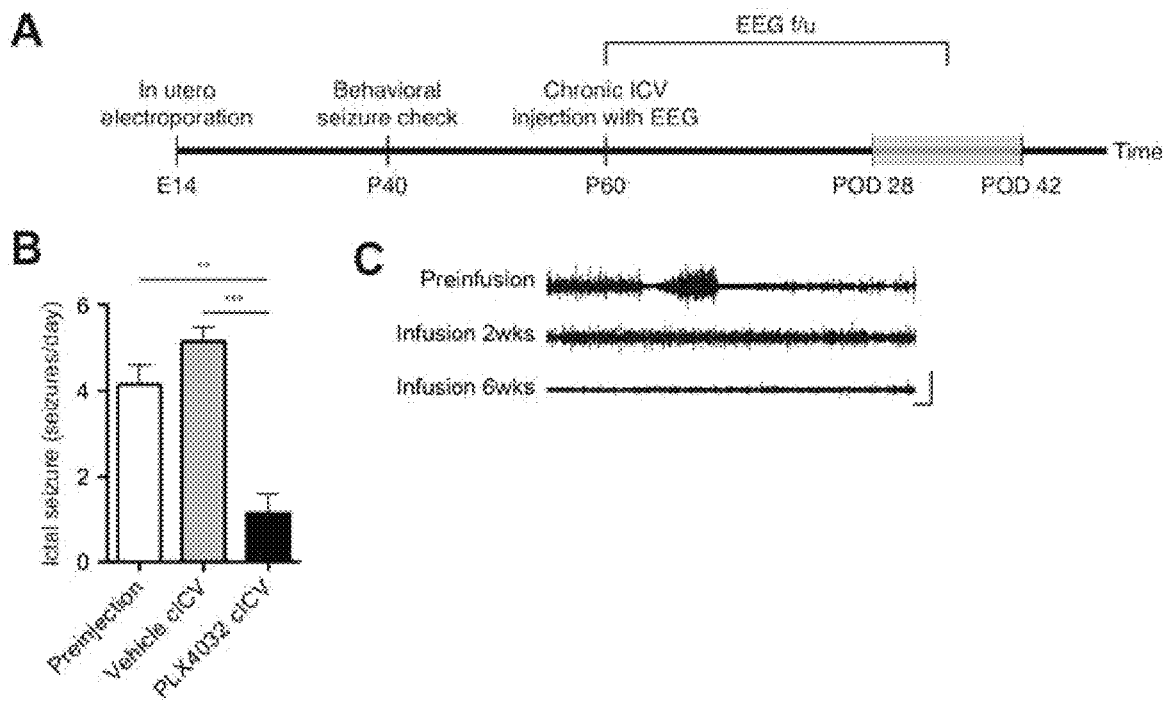
[FIG. 16]
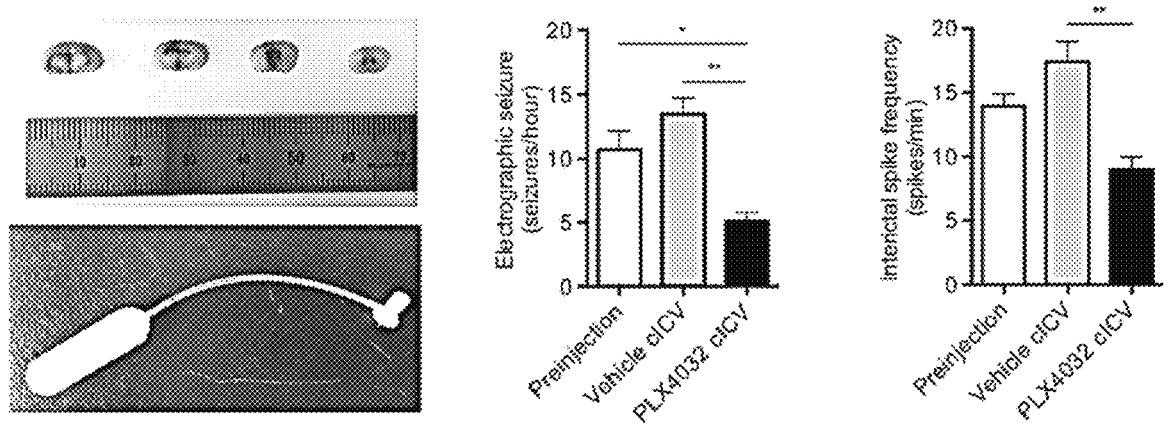

[FIG. 17]
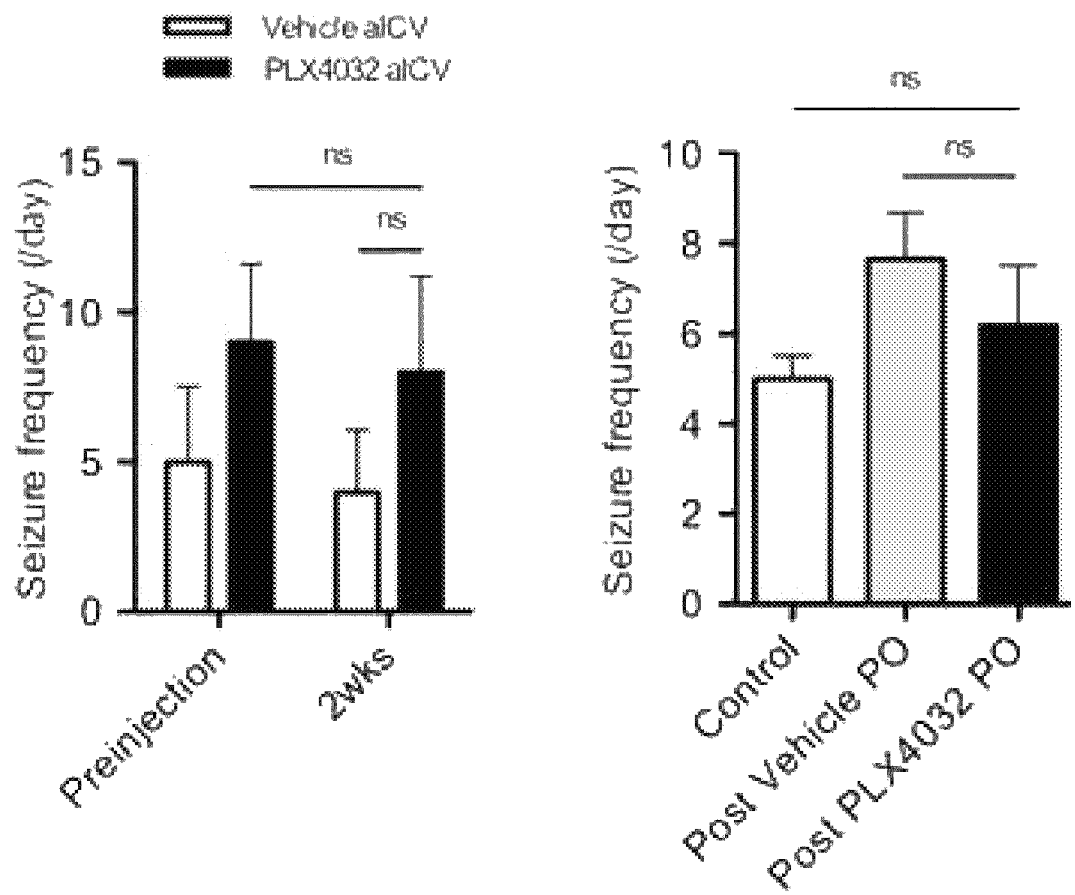

[FIG. 18]
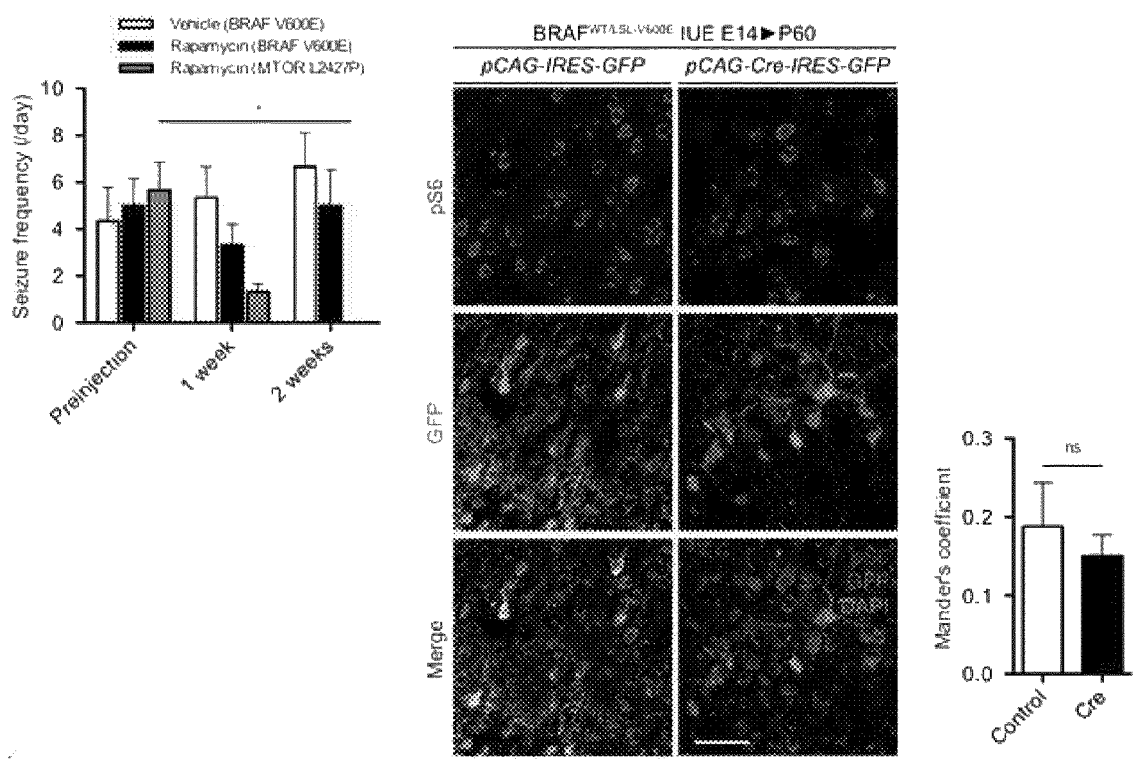

GANGLIOGLIOMA-INDUCED ANIMAL MODEL AND A METHOD FOR DIAGNOSING AND TREATING GANGLIOGLIOMA AND RELATED DISEASES

TECHNICAL FIELD

The present invention relates to a use for diagnosis and treatment of ganglioglioma using a biomarker of ganglioglioma, and specifically, relates to a composition of diagnosing ganglioglioma comprising a BRAF mutant protein and a nucleic acid molecule, and an agent capable of detecting the protein or nucleic acid molecule, a ganglioglioma-induced animal transformed with the BRAF mutant nucleic acid molecule, and a composition for prevention or treatment of ganglioglioma comprising a BRAF mutant protein activity inhibitor.

BACKGROUND ART

Epilepsy is a group of chronic diseases in which an epileptic seizure is repeatedly caused by excessive electricity spasmodically caused by some nerve cells in a short period of time, and is a serious neurological disease accompanying neurobiological, psychological, cognitive and social changes.

Epilepsy is the third most common neurological disease following Alzheimer and stroke, with about 0.5%-2% of the world's population suffering from epilepsy. In addition, there are 45 new patients per 100,000 people worldwide each year, and in Korea, it is estimated that there are about 300,000 to 400,000 epileptic patients, and it is reported that about 20,000 new epileptic patients occur every year. Furthermore, it is known that 70% of all cases of epilepsy occur in the age of pediatric adolescents, and in particular, the incidence is higher in infancy. The incidence and prevalence are in the form of U-shaped, which are highest in the first year of life, but rapidly decrease, and rapidly increase again in elderly people over 60 years of age, and the prevalence of experiencing a seizure in lifetime is 10 to 15%.

Among the epilepsy, epilepsy which does not respond to anti-epileptic drugs developed until now is called intractable epilepsy, accounting for about 40% of the total epilepsy.

As causative diseases of epilepsy, malformations of cortical developments (MCD), ganglioglioma (GG) and hippocampal sclerosis (HS), or Sturge weber syndrome (SWS) and the like are known.

Ganglioglioma is one of important causes of intractable epilepsy that does not respond to drug treatment, accounting for about 80% of childhood intractable epilepsy resulting from tumor. This is the most common nerve cell tumor of the central nervous system, and is a benign tumor with dysplasia in both nerve cell and glia. Most of them occur in pediatric patients, and repeated epilepsy is accompanied as the main symptom in nearly 80% of them. Surgical resection reduces the number of seizures, but there is a problem that an epileptic seizure is persistent in some patients, and in some cases, surgical treatment is difficult, since the age at onset is low and the location of the tumor is deep. In particular, the molecular genetic causes of ganglioglioma are not known, so it is difficult to develop a new and effective treatment of ganglioglioma.

Although previous studies have speculated somatic mutations specific to ganglioglioma, there has not yet been a clear causality between these mutations and onset of ganglioglioma, and therefore whether these somatic mutations actually cause epilepsy and the biological mechanism related thereto are not yet known.

DISCLOSURE

Technical Problem

An object of the present invention is to provide a BRAF mutant protein and a nucleic acid molecule as a biomarker for diagnosing epilepsy.

An additional object of the present invention relates to a composition for diagnosis, a diagnostic kit and a method for diagnosis, of epilepsy comprising an agent capable of detecting a BRAF mutant protein and a nucleic acid molecule.

Other object of the present invention relates to an epilepsy-induced animal transformed with a BRAF mutant nucleic acid molecule, and a composition for screening and a method for screening, of therapeutic drugs of epilepsy or ganglioglioma using the animal.

An additional object of the present invention provides a composition for prevention or treatment of epilepsy and ganglioglioma comprising a BRAF mutant protein activity inhibitor.

Technical Solution

The present inventors have discovered a brain lesion-specific somatic mutation of ganglioglioma using whole exome sequence analysis, for brain tissue samples of ganglioglioma surgery patients, and have prepared an animal model expressing such a brain somatic mutation, and have confirmed that there is an effect of treating epilepsy significantly when an activity inhibitor of BRAF mutant protein is administered into the prepared animal model, thereby completed the present invention.

As one aspect to achieve the above object, the present invention relates to a composition for diagnosing ganglioglioma or epilepsy caused by ganglioglioma, comprising an agent capable of detecting a mutant protein consisting of an amino acid sequence comprising a mutation in which valine at position 600 is substituted to glutamic acid in an amino acid sequence of SEQ ID NO: 1, or an agent capable of detecting a mutant nucleic acid molecule consisting of a nucleotide sequence comprising a mutation in which thymine at position 1799 is substituted to adenine in a nucleotide sequence of SEQ ID NO: 2.

As another aspect, the present invention relates to a method for detecting a protein consisting of an amino acid sequence comprising a mutation in which valine at position 600 is substituted to glutamic acid in an amino acid sequence of SEQ ID NO: 1, or a nucleic acid molecule consisting of a nucleotide sequence comprising a mutation in which thymine at position 1799 is substituted to adenine in a nucleotide sequence of SEQ ID NO: 2, to provide information required for diagnosis of epilepsy.

As other aspect, the present invention relates to a composition for inducing ganglioglioma or epilepsy caused by ganglioglioma, comprising a protein consisting of an amino acid sequence comprising a mutation in which valine at position 600 is substituted to glutamic acid in an amino acid sequence of SEQ ID NO: 1.

As other aspect, the present invention relates to a recombinant vector, comprising a nucleic acid molecule comprising a mutation in which thymine at position 1799 is substituted to adenine in a nucleotide sequence of SEQ ID NO: 2.

As other aspect, the present invention relates to a cell introduced by a recombinant vector comprising a nucleic acid molecule comprising a mutation in which thymine at position 1799 is substituted to adenine in a nucleotide sequence of SEQ ID NO: 2 is introduced.

As other aspect, the present invention relates to an animal or an embryo of the animal, in which a recombinant vector comprising a nucleic acid molecule comprising a mutation in which thymine at position 1799 is substituted to adenine in a nucleotide sequence of SEQ ID NO: 2 is introduced.

As other aspect, the present invention relates to an animal with an induced ganglioglioma or epilepsy caused by ganglioglioma, wherein the animal is transformed with a recombinant vector comprising a nucleic acid molecule comprising a mutation in which thymine at position 1799 is substituted to adenine in a nucleotide sequence of SEQ ID NO: 2.

As other aspect, the present invention relates to a method for preparing an animal with an induced ganglioglioma or epilepsy caused by ganglioglioma, comprising preparing a recombinant vector comprising a nucleic acid molecule comprising a mutation in which thymine at position 1799 is substituted to adenine in a nucleotide sequence of SEQ ID NO: 2; and transforming a mouse with the recombinant vector.

As other aspect, the present invention relates to a screening method of a therapeutic agent for ganglioglioma or epilepsy caused by ganglioglioma, comprising determining an alleviation of epilepsy after administering a candidate substance for epilepsy treatment into an animal with an induced ganglioglioma or epilepsy caused by ganglioglioma.

As other aspect, the present invention relates to a composition for preventing or treating ganglioglioma or epilepsy caused by ganglioglioma comprising an activity inhibitor of a protein comprising an amino acid in which valine at position 600 is substituted to glutamic acid in an amino acid sequence of SEQ ID NO: 1.

Hereinafter, the present invention will be described in more detail.

The present invention relates to a biomarker for diagnosis of intractable epilepsy, for example, intractable epilepsy caused by ganglioglioma (GG), using a brain lesion-specific somatic mutation of ganglioglioma.

The present invention relates to a biomarker for diagnosing epilepsy and its use. More specifically, the present invention relates to BRAF gene in which sequence mutation occurs or BRAF protein in which amino acid sequence mutation occurs by sequence mutation. In addition, the present invention relates to a composition and a kit for diagnosing epilepsy comprising an agent capable of detecting the gene or the protein. Furthermore, the present invention relates to a method for detecting the gene and protein that are biomarkers for diagnosis epilepsy from a sample of a patient, in order to provide information required for diagnosis of epilepsy.

Herein, the term "epilepsy" means a chronic disease-causing seizure repeatedly as some of nerve cells cause excessive electricity in a short time. Herein, the epilepsy may include intractable epilepsy, and the epilepsy may be intractable epilepsy caused by ganglioglioma (GG).

The present inventors have analyzed brain tissue samples after surgery of ganglioglioma (GG) patients accompanying intractable epilepsy having no medicinal effects in conventional antiepileptics among pediatric patients having low grade glioma, based on the correlation that pediatric low grade brain tumor accompanies intractable epilepsy with a high percentage which is different from adult brain tumor, based on the conventional cancer public data analysis, and as a result, the present inventors have confirmed that BRAF V600E brain somatic mutation, in which the valine of 600th amino acid of BRAF protein consisting of the amino acid sequence of SEQ ID NO: 1 is substituted to glutamic acid (hereinafter, BRAF V600E) is specifically present, and the present inventors have confirmed that the BRAF V600E amino acid and a gene encoding the amino acid may be used as a biomarker panel for diagnosing brain tumor-derived pediatric intractable epilepsy.

The BRAF V600E mutation was not found in blood of patients, and it was specifically found in the brain tissue samples. In addition, it has been confirmed that the genetic mutation ratio is 30 to 70% in the ganglioglioma patient group, and the ratio of the mutant gene to the normal allele present in each patient is 5% to 35% (Table 3).

The tumor used in the experiment is a benign tumor and because the copy number of mutant cells is small, as a result of confirmation by whole exome sequence analysis, any other mutations other than BRAF V600E mutation was not found. In other words, it has been confirmed that only the BRAF V600E single mutation is related to ganglioglioma, and thus it has been confirmed that BRAF V600E has a very strong correlation with phenotypes shown in ganglioglioma patients (Example 2).

The intractable epilepsy of the present invention may be caused by ganglioglioma, and specifically, ganglioglioma may be brain somatic mutation-related ganglioglioma, and preferably, the brain somatic mutation may be brain somatic BRAF V600E mutation, but not limited thereto.

Herein, the term "brain somatic mutation" means that mutation of a sequence occurs in one or more positions in a wildtype gene. For example, it may be an amino acid mutation of BRAF genes or protein corresponding to these genes.

The ganglioglioma or epilepsy caused by ganglioglioma may not be caused by activation of the mTOR signaling pathway, and the ganglioglioma or epilepsy caused by ganglioglioma may be caused by expression of the mutant protein or the mutant nucleic acid molecule in nerve cells, not glia, and the ganglioglioma or epilepsy caused by ganglioglioma may be caused by expression of the mutant protein or the mutant nucleic acid molecule in nerve cells at an embryo development stage, but not limited thereto.

The embryo development stage may mean a time to a gastrula stage, and specifically, it may mean a time before organ is formed.

The BRAF gene or protein has been known as a protein kinase playing a role in delivering signals of cell division from a cell membrane to a nucleus, and it functions to deliver MAP kinase signals by phosphorylating MEK kinase and ERK kinase. The amino acid sequence of human BRAF is described in SEQ ID NO: 1, and the NCBI accession number of SEQ ID NO: 1 is NP_004324.2, and the sequence encoding SEQ ID NO: 1 is described in SEQ ID NO: 2, and the NCBI accession number of SEQ ID NO: 2 is NM_004333.4. The amino acid sequence of mouse (Mus musculus) BRAF corresponding to the human is described in SEQ ID NO: 3, and the NCBI accession number of SEQ ID NO: 3 is NP_647455.3, and the sequence encoding SEQ ID NO: 3 is described in SEQ ID NO: 4, and the NCBI accession number of SEQ ID NO: 4 is NM_139294.5.

Herein, a preferable example of the brain somatic mutation means a mutation of the amino acid sequence of SEQ ID NO: 1 which is a wildtype human BRAF gene. For example, it means a protein consisting of an amino acid sequence comprising a mutation in which valine at position 600 is substituted to glutamic acid in an amino acid sequence of SEQ ID NO: 1 (BRAF V600E). As another example, herein, the brain somatic mutation may be a nucleic acid molecule consisting of a nucleotide sequence comprising a mutation in which thymine at position 1799 is substituted to adenine in a nucleotide sequence of SEQ ID NO: 2 which is a sequence encoding wildtype BRAF protein.

The mutation of mouse BRAF corresponding to human BRAF may mean a protein consisting of an amino acid sequence comprising a mutation in which the 637th valine is substituted to glutamic acid in the amino acid sequence of SEQ ID NO: 3 (BRAF V637E), and may be a nucleic acid molecule consisting of a nucleotide sequence comprising a mutation in which the 1910th thymine is substituted to adenine in the nucleotide sequence of SEQ ID NO: 4.

In one example of the present invention, in order to produce mice expressing the mutation of BRAF, a protein consisting of an amino acid sequence comprising a mutation in which the 637th valine is substituted to glutamic acid in the amino acid sequence of SEQ ID NO: 3 (BRAF V637E), or a nucleic acid molecule consisting of a nucleotide sequence comprising a mutation in which the 1910th thymine is substituted to adenine in the nucleotide sequence of SEQ ID NO: 4 was used.

However, mouse BRAF V637E is traditionally represented by BRAF V600E as same as human BRAF V600E, so in the present description, for mice expressing the mouse BRAF V637E mutation, it is described as BRAF V600E.

In addition, the mutant protein may comprise an additional mutation within a range which does not modify the activity of the molecule totally. The exchange of an amino acid in a protein and a peptide which does not modify the activity of a molecule totally has been known in the art (H. Neurath, R. L. Hill, The Proteins, Academic Press, New York, 1979). Occasionally, the BRAF mutant protein may be under modification by phosphorylation, sulfation, acrylation, glycosylation, methylation, farnesylation and the like.

The present invention relates to a composition for diagnosing ganglioglioma or epilepsy caused by ganglioglioma, comprising an agent capable of detecting a mutant protein consisting of an amino acid sequence comprising a mutation in which valine at position 600 is substituted to glutamic acid in an amino acid sequence of SEQ ID NO: 1, or an agent capable of detecting a mutant nucleic acid molecule consisting of a nucleotide sequence comprising a mutation in which thymine at position 1799 is substituted to adenine in a nucleotide sequence of SEQ ID NO: 2.

Herein, the term "diagnosis" means confirming presence or features of pathological conditions. On the purpose of the present invention, diagnosis is to confirm occurrence or possibility of occurrence of ganglioglioma or epilepsy caused by ganglioglioma.

In one example of the present invention, in order to accurately reflect the tumor-derived epilepsy patient model on an animal model, ganglioglioma known as the biggest cause in children was selected as a suitable model disease among epilepsy-related tumors, and brain tissue and blood samples were collected after surgery, and the BRAF V600E mutation was specifically confirmed in the brain tissue samples (Examples 1 and 2), and thereby it was confirmed that the BRAF V600E mutation is usable as a marker for diagnosis of epilepsy, and preferably it is usable as a marker for diagnosis of ganglioglioma or epilepsy caused by ganglioglioma.

Herein, "agent capable of detecting a gene" means a substance which can be used for detecting the BRAF mutant gene in samples of patients. As one specific example, it may be a primer, a probe, an antisense oligonucleotide and the like, which are complementary to a gene consisting of a nucleotide sequence comprising a mutation in which thymine at position 1799 is substituted to adenine in a nucleotide sequence of SEQ ID NO: 2. The primer, probe or antisense oligonucleotide is preferable to specifically bind to a nucleotide sequence comprising a mutation in which thymine at position 1799 is substituted to adenine in a nucleotide sequence of SEQ ID NO: 2, and not specifically bind to a sequence of other nucleic acid substances.

Then, complementary binding means that an antisense oligonucleotide is sufficiently complementary to be selectively hybridized to a BRAF mutant gene target, under a certain hybridization or annealing condition, preferably a physiological condition, and it has a meaning of including both substantially complementary and perfectly complementary ones, and preferably, it means perfectly complementary one.

As one example, the agent used for detecting the BRAF mutant gene biomarker of the present invention may be an antisense nucleotide.

The term "antisense nucleotide" means a molecule based on a nucleic acid which can form a dimer with the BRAF mutant gene as it has a sequence complementary to the targeted BRAF mutant gene, and it may be used for detecting the BRAF mutant gene biomarker of the present invention.

As other example, the agent used for detecting the BRAF mutant gene biomarker of the present invention is a primer pair or probe, and because the sequence of the BRAF mutant gene is discovered in the present description, those skilled in the art may design a primer or probe which specifically amplifies a certain region of this gene based on the sequence.

The term "primer" is a nucleic acid sequence having a free 3' hydroxyl group and it means a nucleic acid sequence of 7 to 50, which can form a base pair with a complementary template and function as a starting point for template strand copy. The primer is commonly synthesized, but naturally produced nucleic acids may be used. The sequence of the primer is not necessary to be accurately same as the sequence of the template, and it is enough to be hybridized with the template because it is sufficiently complementary. Preferably, the primer of the present invention may be a primer which can amplify the BRAF mutant gene.

As other example, the agent used for detecting the BRAF mutant gene biomarker of the present invention may a probe.

The term "probe" means a nucleic acid fraction of RNA or DNA and the like corresponding to short several bases to long hundreds of bases, and the presence or absence of specific mRNA can be confirmed as it is labeled. The probe may be prepared in a form of oligonucleotide probe, single stranded DNA probe, double stranded DNA probe, RNA probe and the like.

In the present invention, hybridization is conducted using a probe complementary to the BRAF genetic mutation, thereby diagnosing through hybridization. Selection of a proper probe and hybridization conditions may be modified based on those known in the art.

Herein, "agent capable of detecting protein" means a substance which can be used for detecting BRAF mutant protein in samples of patients. Preferably, it may be a certain compound or synthetic substance targeting the BRAF mutant protein. As one specific example, it may be an antibody or aptamer specific to the protein consisting of an amino acid sequence comprising a mutation in which valine at position 600 is substituted to glutamic acid in an amino acid sequence of SEQ ID NO: 1. Preferably, the antibody may be a monoclonal antibody or polyclonal antibody.

The term "antibody" means a specific protein molecule indicated for an antigenic site as the term known in the art. On the purpose of the present invention, the antibody means an antibody which specifically binds to the BRAF mutant protein that is the marker of the present invention, and this antibody may be prepared by common methods from the obtained BRAF mutant protein, after the BRAF mutant gene is cloned into an expression vector according to common methods and BRAF mutant protein which is encoded by the BRAF mutant gene is obtained. It includes a partial peptide which can be produced from the BRAF mutant protein, and the partial peptide of the present invention includes at least 7 amino acids, preferably 9 amino acids, more preferably 12 or more amino acids. The form of the antibody of the present invention is not particularly limited, and the antibody of the present invention includes a polyclonal antibody, a monoclonal antibody or parts having antigen-binding thereof, and all immunoglobulin antibodies are included. Moreover, the antibody of the present invention includes a special antibody such as a humanized antibody.

The antibody used for detection of the biomarker for diagnosing epilepsy of the present invention includes not only a complete form having 2 of whole length of light chains and 2 of whole length of heavy chains, but also functional fractions of the antibody molecule. The functional fractions of the antibody molecule mean fractions retaining at least a function of binding to an antigen and there are Fab, F(ab'), F(ab') 2 and Fv and the like.

In addition, the composition for diagnosing epilepsy comprising an agent capable of detecting BRAF mutant gene or BRAF mutant protein of the present invention may be provided as materialized in a form of kit.

The kit of the present invention can detect the biomarkers for diagnosing epilepsy, BRAF mutant gene or BRAF mutant protein. The kit of the present invention may comprise not only a primer, a probe or an antisense oligonucleotide for detecting the BRAF mutant gene or BRAF mutant protein, or an antibody recognizing the BRAF mutant protein selectively, but also one kind or more kinds of other constituent composition, solution or device appropriate for analysis.

As one specific example, in the present invention, the kit for detecting the BRAF mutant gene may be a kit for diagnosing epilepsy comprising essential elements necessary to perform a DNA chip. The DNA chip kit may comprise a substrate in which a gene or cDNA corresponding to its fragment is attached with a probe, and a reagent, an agent, or enzyme for producing a fluorescent labeled probe and the like. In addition, the substrate may comprise a quantitative control gene or cDNA corresponding to its fraction. Moreover, the kit for detecting the BRAF mutant gene may be a kit comprising essential elements necessary to perform PCR. The PCR kit may comprise a test tube or other appropriate container, a reaction buffer solution (various pH and magnesium concentrations), deoxynucleotides (dNTPs), an enzyme such as Taq-polymerase, DNase, RNAse inhibitor, DEPC-water, sterile water and the like, in addition to each primer pair specific to the BRAF mutant gene. Furthermore, it may comprise a primer pair specific to a gene used as a quantitative control group.

As other specific example, in the present invention, the kit for detecting the BRAF mutant protein may comprise a substrate, a proper buffer solution, a coloring enzyme or a secondary antibody labelled with a fluorescent substance, a coloring substrate and the like, for immunological detection of an antibody. As the substrate, nitrocellulose film, a 96 well plate synthesized by polyvinyl resin, a 96 well plate synthesized by polystyrene, and a slide glass made of glass and the like may be used, and as the coloring enzyme, peroxidase and alkaline phosphatase may be used, and as the fluorescent substance, FITC, RITC and the like may be used, and as the coloring substrate solution, ABTS (2,2'-azino-bis (3-ethylbenzothiazolne-6-sulfonic acid)) or OPD (o-phenylene diamine), TMB (tetramethyl benzidine) may be used.

The present invention relates to a method for detecting a protein consisting of an amino acid sequence comprising a mutation in which valine at position 600 is substituted to glutamic acid in an amino acid sequence of SEQ ID NO: 1, or a nucleic acid molecule consisting of a nucleotide sequence comprising a mutation in which thymine at position 1799 is substituted to adenine in a nucleotide sequence of SEQ ID NO: 2, to provide information required for diagnosing epilepsy.

The method for detecting a nucleic acid molecule may comprise amplifying a nucleic acid from a sample of a patient, and determining the sequence of the amplified nucleic acid.

The sample may be a brain tissue sample of a patient, but not limited thereto.

As one aspect to conduct the present invention, in order to provide information required for diagnosing epilepsy, a method for detecting the BRAF mutant gene or BRAF mutant protein from a sample of a patient is provided.

More specifically, it may be performed as the method for detecting the BRAF mutant gene or BRAF mutant protein, and separation of genome DNA or total protein from a sample of a patient may be performed using a known process.

Herein, the term "sample of a patient" includes samples such as tissue and cells capable of detecting the BRAF mutant gene or BRAF mutant protein. Preferably, it may be brain tissue, but not limited thereto.

Preferably, the method for detecting the BRAF mutant gene from a sample of a patient may be performed by the method comprising amplifying a nucleic acid from a sample of a patient, and determining the sequence of the amplified nucleic acid.

Specifically, the amplifying a nucleic acid, may be performed by polymerase chain reaction (PCR), multiplex PCR, touchdown PCR, hot start PCR, nested PCR, booster PCR, real-time PCR, differential display PCR (DD-PCR), rapid amplification of cDNA ends (RACE), inverse polymerase chain reaction, vectorette PCR, TAIL-PCR (thermal asymmetric interlaced PCR), ligase chain reaction, repair chain reaction, transcription-mediated amplification, self-retaining sequence replication or selective amplification reaction of a target sequence.

In addition, the determining the sequence of the amplified nucleic acid, may be performed by Sanger sequencing, Maxam-Gilbert sequencing, Shotgun sequencing, pyrosequencing, hybridization by microarray, allele specific PCR, dynamic allele-specific hybridization (DASH), PCR extension analysis, TaqMan method, automatic sequence analysis or next generation sequencing. The next generation sequencing may be conducted using a sequence analysis system widely used in the art, and for example, 454 GS FLX of Roche Company, Genome Analyzer of Illumina Company, SOLid Platform of Applied Biosystems Company and the like may be used.

As other example, the method for detecting the BRAF mutant protein from a sample of a patient includes western blot, ELISA, radioimmunoassay, radioimmunodiffusion, Ouchterlony immunodiffusion method, Rocket immunoelectrophoresis, immunohistological staining, immunoprecipitation assay, complement fixation assay, FACS, protein chip and the like, but not limited thereto. Through the analysis methods, an antigen-antibody complex between the BRAF mutant protein and an antibody against it can be confirmed, and the antigen-antibody complex between the BRAF mutant protein and an antibody against it is determined, thereby diagnosing epilepsy.

Herein, "antigen-antibody complex" means a combination of the BRAF mutant protein and an antibody specific thereto, and formation of the antigen-antibody complex can be measured through signals of a detection label. This detection label may be selected from the group consisting of enzyme, fluorescent materials, ligands, luminous materials, microparticles, redox molecules and radioactive isotopes, but not limited thereto.

As one specific example, the measurement of the antigen-antibody complex between the BRAF mutant protein and an antibody against it is using ELISA method. In addition, preferably, it is to use a protein chip in which one or more antibodies against the BRAF mutant protein are arranged on the designated locations on a substrate and are fixed with a high density. The method for analyzing a sample using a protein chip can confirm occurrence of epilepsy by separating a protein from a sample, hybridizing the separated protein with a protein chip to form an antigen-antibody complex, and reading it to confirm presence of the protein.

Preferably, the method for detecting the BRAF mutant protein from a sample of a patient may be conducted by the method comprising separating the whole protein from a sample of a patient; and analyzing the amino acid sequence of the separated protein and comparing it to a reference sequence. In addition, preferably, it may be conducted by the method for measuring activation of the BRAF protein increased by BRAF genetic mutation. When the BRAF mutant gene or BRAF mutant protein is detected, through the above detecting methods, epilepsy may be diagnosed.

The present invention relates to a BRAF V600E recombinant vector, comprising a nucleic acid molecule consisting of a nucleotide sequence comprising a mutation in which thymine at position 1799 is substituted to adenine in a nucleotide sequence of SEQ ID NO: 2.

In one example of the present invention, a gene in which the 1910th thymine is substituted to adenine in the nucleotide sequence of SEQ ID NO: 4 was amplified using the known site-directed mutagenesis method, and this was linked to the Cre recombinase-dependent loxP sequence, and then conditional mutant transgenic mice expressing the Cre-dependent BRAF V600E protein were prepared with a homologous recombination method by adding it to a mouse embryo, and at the 14th day of pregnancy of the mouse obtained by mating the prepared mouse and tdTomato mouse, the uterine horn was exposed and a Cre recombinase was injected into lateral ventricles of each embryo (introduction of gene in uterus), and thereby an epilepsy-induced mouse expressing the BRAF V600E mutation by the Cre recombinase was produced.

The mouse may express BRAF V637E protein in which the 637th valine is substituted to glutamic acid in the amino acid sequence of SEQ ID NO: 3, or the mouse may express a gene in which the 1910th thymine is substituted to adenine in the nucleotide sequence of SEQ ID NO: 4.

However, mouse BRAF V637E is traditionally represented by BRAF V600E as same as human BRAF V600E, so in the present description, the mouse BRAF V637E mutation is described as BRAF V600E.

The prepared recombinant vector may be a vector which can be expressed in mammals or rodents.

The present invention relates to a composition for inducing ganglioglioma or epilepsy caused by ganglioglioma, comprising a protein consisting of an amino acid sequence comprising a mutation in which valine at position 600 is substituted to glutamic acid in an amino acid sequence of SEQ ID NO: 1.

The composition for inducing ganglioglioma or epilepsy caused by ganglioglioma is characterized by comprising a protein consisting of an amino acid sequence comprising a mutation in which valine at position 600 is substituted to glutamic acid in an amino acid sequence of SEQ ID NO: 1, which is a mutant protein specifically found in ganglioglioma or epilepsy caused by ganglioglioma. The protein consisting of an amino acid sequence comprising a mutation in which valine at position 600 is substituted to glutamic acid in an amino acid sequence of SEQ ID NO: 1 may be encoded by a nucleotide sequence comprising a mutation in which thymine at position 1799 is substituted to adenine in a nucleotide sequence of SEQ ID NO: 2.

Herein, the term "inducing" means inducing a change from a normal condition to a pathological condition. On the purpose of the present invention, inducing is a change from a condition without epilepsy to a condition with epilepsy. Specifically, epilepsy may be induced by injecting a composition comprising a protein consisting of an amino acid sequence comprising a mutation in which valine at position 600 is substituted to glutamic acid in an amino acid sequence of SEQ ID NO: 1. In addition, epilepsy may be induced by injecting a composition comprising a gene consisting of a sequence comprising a mutation in which thymine at position 1799 is substituted to adenine in a nucleotide sequence of SEQ ID NO: 2, but not limited thereto, epilepsy may be induced by injecting the protein of SEQ ID NO: 1 in which the amino acid sequence is mutated or the gene of SEQ ID NO: 2 in which the gene sequence is mutated.

The ganglioglioma or epilepsy caused by ganglioglioma may not occur by activation of the mTOR signaling pathway, and the ganglioglioma or epilepsy caused by ganglioglioma may occur by expression of the mutant protein or the mutant nucleic acid molecule in nerve cells not glia, and the ganglioglioma or epilepsy caused by ganglioglioma may occur by expression of the mutant protein or the mutant nucleic acid molecule in nerve cells at an embryo development stage, but not limited thereto.

The embryo development stage may mean a time to a gastrula stage, and specifically, it may mean a time before organ is formed.

In one example of the present invention, it was confirmed that the ganglioglioma or epilepsy caused by ganglioglioma was independent on the BRAF V600E mutation originated from glia, and the BRAF V600E mutation occurring in nerve cells played an important role in an epilepsy occurrence mechanism, and it was confirmed that when the BRAF V600E mutation occurred only in glia, glia proliferation ability and benign tumors increased. Through the above result, it could be seen that the ganglioglioma or epilepsy caused by ganglioglioma of the present invention occurred by the BRAF V600E mutation occurring in nerve cells, but the BRAF V600E occurring in glia did not induce the ganglioglioma nor epilepsy caused by ganglioglioma of the present invention, but induced proliferation of cells (Example 6).

In one example of the present invention, it was confirmed that the ganglioglioma or epilepsy caused by ganglioglioma was not induced by the BRAF V600E mutation expressed in adulthood, but it was induced by the BRAF V600E mutation expressed at the embryo development stage before the organogenesis stage (Example 5).

In addition, in one example of the present invention, it was confirmed that the ganglioglioma or epilepsy caused by ganglioglioma was not induced by the mTOR signaling pathway (Example 9).

The present invention may be a recombinant vector, comprising a nucleic acid molecule comprising a mutation in which thymine at position 1799 is substituted to adenine in a nucleotide sequence of SEQ ID NO: 2.

The present invention relates to a cell in which a recombinant vector comprising a nucleic acid molecule comprising a mutation in which thymine at position 1799 is substituted to adenine in a nucleotide sequence of SEQ ID NO: 2 is introduced. The cell may be a brain cell.

The present invention relates to an embryo in which a recombinant vector comprising a nucleic acid molecule comprising a mutation in which thymine at position 1799 is substituted to adenine in a nucleotide sequence of SEQ ID NO: 2 is introduced.

The embryo may be a mammal except for a human or a rodent, and the embryo may be an embryo at a brain formation or development stage.

The present invention relates to an animal except for a human, which is transformed with a recombinant vector comprising a nucleic acid molecule comprising a mutation in which thymine at position 1799 is substituted to adenine in a nucleotide sequence of SEQ ID NO: 2 and thereby ganglioglioma or epilepsy caused by ganglioglioma is induced in.

The present invention relates to a transgenic animal transformed by the recombinant vector.

Herein, the term "transgenic animal" means an animal in which modification of traits is induced so that the BRAF V600E protein activity is increased in cells compared to a normal cell, and transformation may be induced by flowing in the vector expressing the BRAF protein in which the amino acid sequence is mutated in cells. The transgenic animal in which epilepsy occurs may be effectively used as an epilepsy animal model.

The animal may be a mammal except for a human or a rodent, and it may be one in which ganglioglioma or epilepsy caused by ganglioglioma is induced.

The present invention relates to a method for producing an animal with an induced ganglioglioma or epilepsy caused by ganglioglioma, comprising preparing a recombinant vector comprising a nucleic acid molecule comprising a mutation in which thymine at position 1799 is substituted to adenine in a nucleotide sequence of SEQ ID NO: 2; and
transforming a mouse with the recombinant vector.

The method for introducing the recombinase vector is not particularly limited. For example, through methods such as transformation, transfection or transduction and the like, the vector may be inserted into a cell. The vector inserted into a cell may produce the BRAF protein in which the amino acid sequence is mutated by consistent gene expression in the cell.

The recombinant vector may be introduced into brain of an embryo in a period of formation of a cerebral cortical layer in the embryonic period, but not limited thereto.

In one specific example of the present invention, a conditional mutant transgenic mouse capable of expressing a gene in which the 1910th thymine is substituted to adenine in the nucleotide sequence of SEQ ID NO: 4 in a Cre-dependent manner was prepared, and a plasmid having a Cre recombinase was introduced in uterus of the mouse to prepare an epilepsy-induced mouse animal model.

The present invention relates to an epilepsy-induced animal which is transformed with a recombinant vector comprising a sequence encoding an amino acid in which valine at position 600 is substituted to glutamic acid in an amino acid sequence of SEQ ID NO: 1. The animal may be a mammal except for a human or a rodent.

Herein, "animal model" or "disease model" means an animal to be a model which can be an object of study capable of investigating causes of a disease and confirming pathological conditions, as it has a specific disease similar to a disease of a human. The animal to be used as the animal model may have a predicted effect same as a human and may be easily produced and has reproducibility. In addition, it should be progressed as same or similar to causes of a human disease. Thus, an animal which is a mammal vertebrate like a human, and has similar internal structure, immune system, body temperature and the like with human, and suffers from a disease such as high blood pressure, cancer, immunodeficiency, and the like, is appropriate. Such an animal may be preferably a mammal such as horse, ship, pig, goat, camel, antelope, dog, rabbit, mouse, rat, guinea pig, hamster, and the like, and more specifically, it may be a rodent such as mouse, rat, guinea pig, hamster and the like.

In one example of the present invention, it was confirmed that BRAF V600E had a very strong correlation to phenotypes shown in ganglioglioma patients, and based on this, it was confirmed whether phenotypes of epilepsy were shown in the animal model when a normal BRAF gene was substituted to the BRAF V600E mutation (Example 4).

In one example of the present invention, before confirming whether phenotypes of epilepsy was shown in the BRAF gene substitution model, patient tissues were stained with a marker specific to nerve cells and a marker specific to glia, respectively, and only the cells in a specific tissue form were separated using a method of laser capture microscope anatomy to confirm presence or absence of the BRAF V600E mutation, thereby confirming that the BRAF V600E mutation was originated from both nerve cell and glia-based cell lines (FIG. 2a and FIG. 2b). Through the above result, it could be inferred that the BRAF V600E mutation occurred in a common ancestor of both nerve cells and glia (Example 3).

In one example of the present invention, as a result of conducting Video-Electroencephalography (video-EEG) surveillance from the 3rd week after birth, after an embryo obtained by electroporation of a plasmid having a Cre recombinase into the lateral ventricle of embryonic mice at 14th day (E14), a spontaneous seizure accompanying an epilepsy wave was confirmed in mice in which a plasmid in which a mutant gene with the sequence mutation of the present invention was inserted (FIGS. 3b and 3c). Furthermore, as a result of cutting brain of the animal model mice and measuring the activity of tissue using a multichannel electrode analysis device, it was confirmed that synchronized burst firing (FIG. 3c) was shown in which spontaneous activity waves and temporally short period of high amplitude energy are simultaneously emitted from several channels, which are distinctive to epilepsy in the brain tissue having the BRAF V600E mutation, different from the control group (Example 4).

In one example of the present invention, it was confirmed that in case of GFP positive cells of cerebral region in which the BRAF V600E mutation was induced by electroporation, dysplasia of nerve cells distinctively shown in ganglioglioma was accompanied, and the size of cells became bigger (FIG. 5a), and the shape of cells were dented (FIG. 5b), and the shape of cells and arrangement of branches of nerve cells were arranged in any direction different to normal nerve cells (FIG. 5c).

In addition, in one example of the present invention, in order to trace daughter cells of neural progenitor cells having the BRAF V600E mutation, as a result of tracing the daughter cells by mating with a conditional floxed tdTomato mouse and preparing a plasmid gene having a Cre recombinase using a method of gene introduction (FIG. 6a), it was confirmed that in the neural progenitor cells having the BRAF V600E mutation, glia-related astrocytes or oligodendrocytes were significantly increased compared to normal brain tissue (FIG. 6b) (Example 5).

Through the above results, it could be seen that mice produced by the method of the present method were appropriate as an animal model in which ganglioglioma was induced, as dysplasia of nerve cells and numerical increment of glia that were features of ganglioglioma were observed.

The epilepsy animal model of the present invention may be effectively used in study on gene functions, and study of molecular mechanisms of epilepsy and investigation of novel antiepileptic drugs, and the like.

The present invention relates to a screening method of therapeutic agent for epilepsy comprising determining epilepsy reduction after administering therapeutic candidates for epilepsy into an animal with an induced ganglioglioma or epilepsy caused by ganglioglioma.

After administering therapeutic candidates for epilepsy into the epilepsy-induced animal, a substance reducing epileptic symptoms indirectly or directly may be selected as a therapeutic agent for epilepsy. In other words, under the absence of therapeutic candidates for epilepsy, epileptic symptoms are measured, and under the presence of therapeutic candidates for epilepsy, epileptic symptoms are measured, and both are compared, and then a substance reducing epileptic symptoms in case of presence of therapeutic candidates for epilepsy than symptoms in case of absence of therapeutic candidates for epilepsy may be predicted as a therapeutic agent for epilepsy.

The present invention relates to a composition for preventing or treating ganglioglioma or epilepsy caused by ganglioglioma comprising an activity inhibitor of a protein comprising an amino acid in which valine at position 600 is substituted to glutamic acid in an amino acid sequence of SEQ ID NO: 1.

A specific example of the activity inhibitor of a protein comprising an amino acid in which valine at position 600 is substituted to glutamic acid in an amino acid sequence of SEQ ID NO: 1 may include one or more selected from the group consisting of Vemurafenib or its salt and Dabrafenib or its salt.

The inhibitor may be Vemurafenib or Dabrafenib, and the Vemurafenib is also called PLX4032, PLX4720, or Zelboraf.

In one example of the present invention, it was confirmed that when the BRAF V600E mutation was introduced to cells, the BRAF protein was hyperactivated, and therefore intractable epilepsy could be induced, and it was confirmed that there were effects of prevention, improvement or treatment of intractable epilepsy caused by ganglioglioma (GG), and prevention, improvement or treatment of ganglioglioma (GG) that was a causative disease of intractable epilepsy, when the activity inhibitor of the BRAF V600E protein was administered, by reduction of seizures (Example 8).

The present invention is to provide a composition, a kit or a method for prevention, improvement or treatment of intractable epilepsy and prevention, improvement or treatment of ganglioglioma (GG) that is a causative disease of intractable epilepsy. Preferably, the intractable epilepsy relates to a use for prevention, treatment and/or improvement related to brain somatic mutation-related intractable epilepsy.

The ganglioglioma or epilepsy caused by ganglioglioma may not occur by activation of the mTOR signaling pathway, and the ganglioglioma or epilepsy caused by ganglioglioma may occur by expression of the mutant protein or the mutant nucleic acid molecule in nerve cells, not glia, and the ganglioglioma or epilepsy caused by ganglioglioma may occur by expression of the mutant protein or the mutant nucleic acid molecule in nerve cells at an embryo development stage, but not limited thereto.

The embryo development stage may mean a time to a gastrula stage, and specifically, it may mean a time before organ is formed.

The composition comprising the inhibitor may be characterized by reducing seizures occurring by ganglioglioma or epilepsy caused by ganglioglioma.

Herein, the inhibitor may be Vemurafenib, or Dabrafenib, and the inhibitor may include all derivatives or analogues of the compound and pharmaceutically acceptable salts or hydrates.

The pharmaceutically acceptable salts or hydrates may be salts or hydrates induced from an inorganic acid or organic acid, and as one example, salts may be hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, toluenesulfonic acid, but not limited thereto. The hydrates may mean that Vemurafenib formed by binding to water molecules.

Herein, "treat" may used as a meaning including all of alleviation or improvement of symptoms, reduction of range of disease, delay or alleviation of disease progress, improvement, alleviation or stabilization of disease conditions, partial or complete recovery, survival extension, and any other beneficial treatment outcomes and the like.

The symptoms related to the ganglioglioma or epilepsy caused by ganglioglioma are shown as nerve cells fail to move to a proper region of brain in the brain development process, and spontaneous seizures, behavior seizures, brainwave seizures and abnormal generation of nerve cells in cerebrum and the like may be exemplified.

Thus, the treatment in the present invention may mean reducing the number of spontaneous seizures, behavior seizures or brainwave seizures significantly, and reducing abnormal activity or nerve cells or abnormal signals in cerebrum, by administering a BRAF V600E protein activity inhibitor, for example, Vemurafenib, for patients of ganglioglioma or epilepsy caused by ganglioglioma.

Depending on use aspects and use methods of the pharmaceutical composition of the present invention, an effective dose of the BRAF protein activity inhibitor may be used by adjusting properly according to the choice of those skilled in the art.

As one example, the pharmaceutical composition may comprise the BRAF protein activity inhibitor in an amount of 0.1 to 10% by weight, more preferably 0.5 to 5% by weight, based on the total weight of the total composition.

The BRAF protein activity inhibitor may be comprised in the pharmaceutical composition alone, or a pharmacologically acceptable additive other than it may be further comprised. The pharmaceutically acceptable additive is commonly used in formulation, and includes lactose, dextrose, sucrose, sorbitol, mannitol, starch, acacia gum, calcium phosphate, alginate, gelatin, calcium silicate, microcrystal cellulose, polyvinylpyrrolidone, cellulose, water, syrup, methyl cellulose, methyl hydroxybenzoate, propyl hydroxybenzoate, talc, magnesium stearate, and mineral oil and the like, and in addition, a pharmaceutically acceptable excipient includes a lubricant, a sweetener, a flavoring agent, an emulsifier, a suspension, a preservative and the like, but not limited thereto. In other words, the pharmaceutically acceptable additive which can be added in the pharmaceutical composition of the present invention may be composed by selection of those skilled in the art depending on use purposes without difficulty, and its addition amount may be selected within a range which does not damage the object and effect of the present invention.

The preferable dose for patients of the pharmaceutical composition of the present invention is different depending on condition and body weight of patients, degree of disease, drug form, administration route and period, but it may be appropriately selected by those skilled in the art. However, for a preferable effect, the extract of the present invention is preferably administered in an amount of 1 mg/kg to 1000 mg/kg, preferably 50 mg/kg to 500 mg/kg, more preferably 150 mg/kg to 300 mg/kg a day. The administration may be carried out once or several times a day. Thus, the dose does not limit the scope of the present invention in any way.

The composition of the present invention may be administered in various routes into mammal animals such as rat, mouse, stock, human and the like. All the methods of administration may be predicted, and for example, it may be administered by oral, intrarectal or intravenous, intramuscular, subcutaneous or intracerebroventricular injection.

The present invention relates to a food composition for prevention or improvement of ganglioglioma or epilepsy caused by ganglioglioma, comprising a BRAF protein activity inhibitor, for example, Vemurafenib or its salt, as other aspect.

The food composition may be used together with common components of other food compositions, and it may be used properly according to common methods. The BRAF protein activity inhibitor may be properly determined depending on the use purpose (prevention, health or therapeutic treatment). In general, it may be added in an amount of 0.01 to 10 parts by weight, preferably, 0.05 to 1 part by weight, based on the raw material of active ingredients when preparing the food composition. However, in case of long-term consumption intended for health and hygiene or health control, the amount may be less than the above range.

The food composition may be contained in health food on a purpose for prevention or improvement of ganglioglioma or epilepsy caused by ganglioglioma, and there is no particular limitation on its kind. Examples of food in which the above substance can be added may include meat, sausage, bread, chocolate, candies, snack, crackers, pizza, ramen, other noodles, gum, dairy products including ice cream, various soup, beverage, tea, drink, alcohol beverage and vitamin complexes and the like, and all the functional foods in the common meaning may be included. Besides the above, the food composition of the present invention may further comprise a food acceptable additive. The percentage of this additive is not greatly important, but it is general to select it within the range of 0.01 to 0.1 part by weight per 100 parts by weight of the composition of the present invention.

Advantageous Effects

The present invention relates to a biomarker of epilepsy, a composition for diagnosing epilepsy, an epilepsy-induced animal, and a composition for preventing or treating epilepsy, and specifically, relates to a composition for diagnosing epilepsy comprising a BRAF mutant protein and a nucleic acid molecule, and an agent capable of detecting the protein or nucleic acid molecule, an epilepsy-induced animal transformed with the BRAF mutant nucleic acid molecule, and a composition for prevention or treatment of epilepsy comprising a BRAF mutant protein activity inhibitor, and the composition for preventing or treating epilepsy comprising a BRAF mutant protein activity inhibitor can be used to prevent or treat ganglioglioma, or epilepsy caused therefrom.

BRIEF DESCRIPTION OF DRAWINGS

FIG. 1a is a picture of confirming that BRAF V600E is significantly present in pediatric low grade glioma with statistical significance.

FIG. 1b is a picture of confirming the magnetic resonance imaging opinion of the head of the ganglioglioma patient (GG221) (left) and the histopathological opinion confirming the corresponding lesion in the arrow during surgery (right).

FIG. 1c is a picture of confirming the magnetic resonance imaging opinion of the head before surgery of ganglioglioma patients (GG57, GG163, GG221, GG231, GG249, and GG381).

FIG. 2a is a schematized picture of the experimental method for presence or absence of BRAF V600E mutation in a nerve cell and glia using the laser capture microscope anatomical method.

FIG. 2b is a picture of confirming the presence or absence of BRAF V600E mutation in a nerve cell (left) and glia (right) using the laser capture microscope anatomical method.

FIG. 3a is a picture of confirming that the mouse produced according to one example of the present invention expresses a BRAF V600E mutant gene.

FIG. 3b is a picture of confirming that a spontaneous seizure accompanying epileptic spikes in the mouse in which the plasmid, in which the BRAF V600E mutant gene is inserted, is injected according to one example of the present invention.

FIGS. 3c is a picture of confirming pathological features specific to epilepsy in the brain tissue obtained from the mouse expressing the BRAF V600E mutant protein produced according to one example of the present invention.

FIG. 4 is a picture of confirming that synchronized burst firing is shown in which spontaneous activity waves and temporally short period of high amplitude energy are simultaneously emitted from several channels, in the mouse expressing the BRAF V600E mutant protein produced according to one example of the present invention.

FIG. 5 is a picture of confirming that dysplasia of the nerve cell characteristically shown in ganglioglioma is accompanied, in the mouse expressing the BRAF V600E mutant protein produced according to one example of the present invention.

FIG. 6a is picture showing a process of mating conditional floxed tdTomato mice for tracing daughter cells of neural progenitor cells having BRAF V600E mutation.

FIG. 6b is a picture of confirming that glia-related astrocytes or oligodendrocytes are significantly increased compared to normal brain tissue in the neural progenitor cells having BRAF V600E mutation produced according to one example of the present invention.

FIG. 6c is a picture of magnifying the photograph of tissue of FIG. 6b at high magnification and retaking it.

FIG. 6d is a picture of confirming that CD34 expression is increased by immunohistochemical staining in the actual patient tissue.

FIG. 7 is a picture of confirming that the expression of CD34 is increased in the mouse expressing the BRAF V600E mutant protein produced according to one example of the present invention.

FIG. 8 is a picture showing the immunofluorescent staining opinion (left) and immunohistochemical staining opinion (right) which show the increase of the CD34 marker in the mouse expressing the BRAF V600E mutant protein produced according to one example of the present invention.

FIG. 9 is a picture of observing abnormal lamination of the cortex in the mouse expressing the BRAF V600E mutant protein produced according to one example of the present invention.

FIG. 10 is a picture of confirming that when a mouse model is produced by the method of one example of the present invention, the brain tissue having BRAF V600E mutation has the changed distribution in the upper and lower parts different from normal brain tissue and shows cortical dysplasia. In the picture at the bottom of FIG. 10, this observation was magnified and it was confirmed that there was no change in the amount of the total nerve cells.

FIG. 11 is a picture of confirming that patterns of behavior of epilepsy are not shown, but the number of glia-based cells is increased, in the mouse expressing BRAF V600E mutation produced according to one example of the present invention only in glia.

FIG. 12 is a picture showing the method for producing a BRAF V600E mutant mouse which is inducible using tamoxifen in an adult mouse.

FIG. 13 is a picture showing the method for producing a BRAF V600E mutant mouse which is inducible using a virus in an adult mouse.

FIG. 14 is a picture of confirming the abnormal cytological aspect in the case of inducing BRAF V600E mutation in an adult mouse.

FIG. 15 is a picture of confirming reduction of seizures through chronic intracerebroventricular injection (cICV) of the BRAF V600E-specific inhibitor in the mouse expressing the BRAF V600E mutant protein produced according to one example of the present invention using measurement of interictal spikes through video monitoring brainwave analysis. POD (post operation day) means days after surgery, and ictal seizure means an epileptic seizure.

FIG. 16 is a picture of confirming reduction of seizures through chronic intracerebroventricular injection of the BRAF V600E-specific inhibitor in the mouse expressing the BRAF V600E mutant protein produced according to one example of the present invention using measurement of interictal spikes and electrographic seizure spikes through video monitoring brainwave analysis.

FIG. 17 is a picture of confirming that there was no reduction of seizures in the video monitoring brainwave analysis through chronic intracerebroventricular injection (cICV) of the BRAF V600E-specific inhibitor and oral administration (PO, per oral) in the mouse expressing the BRAF V600E mutant protein produced according to one example of the present invention.

FIG. 18 is a picture of confirming the activation of the mTOR signaling pathway in the mouse expressing the BRAF V600E mutant protein produced according to one example of the present invention.

DETAILED DESCRIPTION OF THE EMBODIMENTS

Hereinafter, the present invention will be described in more detail by the following examples. However, these examples are intended to illustrate the present invention only, but the scope of the present invention is not limited by these examples.

Example 1

Genome Range Profiling Through Genome Public Data Analysis

Pediatric low grade glioma has much different clinical aspects from brain tumor of general adults, and particularly, it is known that the ratio of accompanying epilepsy is high in this patient group. To confirm why epilepsy is caused with high frequency in pediatric low grade glioma, by analyzing genome public data such as TCGA (The Cancer Genome Atlas) and PeCan (Pediatric Cancer Genomic Data Portal), mutant gene types distinguished in adult and pediatric brain tumors were classified.

As a result, as shown in FIG. 1, mutations of genes such as IDH1 and TP53 were present remarkably many in the brain tumor of adults, but BRAF V600E mutation was present significantly many in pediatric low grade glioma with statistical significance.

TABLE 1

| Gene type | Adult brain tumor | Pediatric brain tumor | Pediatric low grade glioma |
|---|---|---|---|
| | Number of patients (n) | | |
| | 283 | 274 | 73 |
| | Number of mutations (percentage %) | | |
| IDH1 | 215(75.97) | 3(1.09) | 1(1.37) |
| TP53 | 128(45.23) | 38(13.87) | 0(0) |
| H3F3A | 0(0) | 47(17.15) | 3(4.11) |
| CIC | 26(9.19) | 1(0.36) | 1(1.37) |
| BRAF | 2(0.71) | 5(1.82) | 19(26.03) |
| ATRX | 16(5.65) | 3(1.09) | 1(1.37) |
| PIK3CA | 2(0.71) | 16(5.84) | 0(0) |
| SMARCA4 | 8(2.83) | 9(3.28) | 0(0) |
| ACVR1 | 0(0) | 16(5.84) | 0(0) |
| NOTCH1 | 14(4.95) | 2(0.73) | 0(0) |
| Total | 411 | 140 | 25 |

Example 2

Confirmation of BRAF V600E Mutation Using Whole Exome Sequencing 2-1. Confirmation of BARF V600E Candidates by Whole Exome Sequencing in 5 Patients To accurately reflect a tumor-derived epilepsy patient model to an animal model, ganglioglioma known as the biggest cause causing epilepsy-related tumor in children was selected, and to sort gene mutations present in the ganglioglioma, brain tissue and blood samples of 5 ganglioglioma patients (named GG29, GG30, GG221, GG231, and GG249) were collected.

In the brain tissue sample of ganglioglioma patients, the whole exome sequencing (deep whole exome sequencing, read depth 630-672) was performed, and the candidate mutation found both algorithms of Strelka and Mutect of the whole exome sequencing simultaneously, BRAF V600E was sorted.

Specifically, a sequencing library was constructed using Agilent library preparation protocols (Agilent Human All Exon 50 Mb kit) provided by the manufacturer for acquisition of data of whole exome sequencing. Sequencing was conducted for the constructed sequencing library using Hiseq2000 (Illumina), and to increase the accuracy of analysis, sequencing was performed with 5 times depth (~500×) of the general sequencing depth.

The data after the sequencing were converted into a file in a form to be analyzed using Broad Institute best practice pipeline (https://www.broadinstitute.org/gatk/) (bam file) and were stored.

TABLE 2

| Sample | Total yield (bp) | Total depth of target site (X) | Average depth of target site (X) |
|---|---|---|---|
| GG221-Blood | 44,917,301,962 | 630.4 | 293.35 |
| GG221-Brain | 39,837,168,006 | 559.1 | 296.33 |
| GG29-Blood | 47,943,121,572 | 579.8 | 327.14 |

TABLE 2-continued

| Sample | Total yield (bp) | Total depth of target site (X) | Average depth of target site (X) |
|---|---|---|---|
| GG29-Brain | 43,394,449,010 | 596.3 | 328.11 |
| GG30-Blood | 43,443,678,228 | 609.0 | 329.51 |
| GG30-Brain | 41,317,104,442 | 609.7 | 341.22 |
| GG231-Blood | 45,607,318,610 | 630.7 | 351.96 |
| GG231-Brain | 42,488,301,048 | 640.0 | 352.19 |
| GG249-Blood | 44,944,663,064 | 669.9 | 360.64 |
| GG249-Brain | 47,736,544,858 | 672.8 | 361.99 |

As a result, as shown in Table 2, it could be confirmed that the BRAF V600E mutation was present commonly in 3 patients of 5 ganglioglioma patients, and mutations of other genes except for BRAF V600E mutation were not observed. The BRAF V600E mutation confirmed in ganglioglioma is a mutation in which the 1799 thymine of human gene BRAF gene of SEQ ID NO: 2 is substituted to adenine, and this is a mutation in which valine (V) at position 600 of human BRAF protein of SEQ ID NO: 1 is substituted to glutamic acid (E).

2-2. Confirmation of BRAF V600E Mutation in Expanded Patient Group

To confirm whether BRAF V600E confirmed as present in 5 ganglioglioma patients in Example 2-1 was present in other patient group, by expanding the patient group, gene mutations present in 12 patients in total (including 5 patients confirmed in Example 2-1 (GG29, GG30, GG221, GG231, and GG249)) were investigated (Table 3).

TABLE 3

| Patient code | Age at surgery (year) | Main opinion | Period of occurrence of epilepsy (year) | Gender | Pathological opinion | Radiologic opinion | Sequencing method | BRAF V600E mutation allele percentage (%) |
|---|---|---|---|---|---|---|---|---|
| GG29 | 14 | Recurrent seizure | 3 | Male | Ganglioglioma in white matter | In the preoperative image, a 1 cm round lesion accompanying edema was located in supramarginal gyrus | Whole exome sequencing | — |
| GG30 | 15 | Tonic intermittent spasmodic seizure | 4 | Male | Low grade glioma accompanying multiple calcification close to ganglioglioma | In the preoperative image, cystic lesion with increased size in thalamus | Whole exome sequencing | — |
| GG54 | 16 | Recurrent seizure | 10 | Female | Low grade glioma close to ganglioglioma | Low grade cortex tumor close to ganglioglioma in left parahippocampal gyrus, fusiform gyrus and onsil | Target panel sequencing | — |
| GG57 | 14 | Long-term intractable epilepsy | 1 | Male | Low grade glioma close to ganglioglioma | 1.4 cm lump ii mesial temporal lobe | Target panel sequencing | 18.50 |
| GG163 | 6 | Long-term intractable epilepsy | 0.5 | Male | Low grade glioma close to ganglioglioma | Cystic lesion increased at T2 in posteromedial temporal lobe | Target panel sequencing | 28.87 |

TABLE 3-continued

| Patient code | Age at surgery (year) | Main opinion | Period of occurrence of epilepsy (year) | Gender | Pathological opinion | Radiologic opinion | Sequencing method | BRAF V600E mutation allele percentage (%) |
|---|---|---|---|---|---|---|---|---|
| GG221 | 6 | Long-term intractable epilepsy | 0.5 | Female | Low grade glioma close to ganglioglioma | 1 cm Cystic lesion in left temporal lobe | Whole exome sequencing | 15.44 |
| GG231 | 7 | Long-term intractable epilepsy | 2 | Male | Low grade glioma close to ganglioglioma | 1.5 cm T2 increased lesion in right uncus | Whole exome sequencing | 17.86 |
| GG249 | 5 | Long-term intractable epilepsy | 1 | Female | Low grade glioma close to ganglioglioma | T2 increased lesion in right temporalis posterior | Whole exome sequencing | 19.05 |
| GG263 | 2 | Recurrent seizure | 1 | Male | Low grade glioma close to ganglioglioma | T2 increased signal in left frontal lobe | Target panel sequencing | — |
| GG351 | 5 | Seizure | 1 | Male | Tumor-related intractable epilepsy close to ganglioglioma | — | Target panel sequencing | — |
| GG356 | 9 | Seizure | 2 | Male | Tumor-related intractable epilepsy close to ganglioglioma | — | Target panel sequencing | — |
| GG381 | 7 | Long-term intractable epilepsy | 1 | Male | Tumor-related intractable epilepsy close to ganglioglioma | 2.8 cm cystic lesion in regions including uncus, parahippocampal gyrus and inferotemporal lobe gyrus | Target panel sequencing | 7.41 |

The BRAF V600E mutation was not found in blood of patients, but was found specifically in the brain tissue sample.

As a result, as could be seen in Table 3, it could be confirmed that the BRAF V600E mutation was present in 6 patients in 12 ganglioglioma patients in total (Genetic variation ratio was 50%), and it could be seen that the ratio of the BRAF V600E mutation allele to the BRAF normal allele present in each patient was about 7 to 30%.

2-3. Patient Sample Collection and Genome DNA Extraction

For 12 patients of intractable epilepsy caused by ganglioglioma (GG) used in Example 2-2, with the consent of all the patients, their brain tissue (1-2 g), saliva (1-2 mL), blood (about 5 mL), frozen tissue and formalin fixed paraffin-embedded brain tissue were obtained (Severance Hospital Pediatric Neurosurgery and Pediatric Neurology). Using the following kits with the manufacturers' protocols, the genome DNA of brain tissue, blood, saliva, frozen and formalin fixed paraffin-embedded brain tissue of patients was separated:

brain tissue: Qiamp mini DNA kit (Qiagen, USA), blood: Flexigene DNA kit (Qiagen, USA), saliva: prepIT2P purification kit (DNAgenotek, USA), frozen tissue and formalin fixed paraffin-embedded brain tissue: Qiamp mini FFPE DNA kit (Qiagen, USA).

2-4. Ganglioglioma-Specific Gene Mutation Sequencing

To further confirm whether the BRAF V600E mutation was present in ganglioglioma patients, for the rest 7 patients except for 5 patients confirmed in Example 2-1 among 12 patients confirmed in Example 2-2, hybrid capture sequencing was performed by the following method so that the lead depth was 100-17,700. For the hybrid capture sequencing, a BRAF gene-specific probe was produced using SureDesign online tools (Agilent Technologies). Using Agilent library preparation protocols provided by the manufacturer, a sequencing library was constructed. For the constructed sequencing library, using Hiseq2500 (illumina), the sequencing was performed so that the central lead depth was 500×. The data after the sequencing were made into a file in a form that could be analyzed using Broad Institute best practice pipeline (https://www.broadinstitute.org/gatk/).

To find a brain tissue-specific de novo somatic mutation, the somatic mutation found in both algorithms of Strelka and Mutect among gene sequencing results of blood and brain tissue simultaneously was selected. In addition, only genetic mutations satisfying screening criteria of 100 or more depth and 3 or more mutated calls (30 or more mapping quality) among genetic mutations all found in the hybrid capture sequencing result were selected as a disease-related gene candidate.

To definitely eliminate errors caused in the sequencing process, only the cases of 1% or more genetic variation rate were considered as positive, and only the cases that all variations were shown when the hybrid capture exome sequencing was performed in the genome DNA of blood and brain tissue were considered as positive, to select these variations as genuine mutations.

As a result, as shown in the following Table 4, the BRAF V600E mutation was not found in the saliva and blood (control group) of genetic variation positive patients (1% or more genetic variation rate) (negative). However, the BRAF V600E mutation was repeatedly detected in 3 patients (GG221, GG231, GG249), and the percentage of BRAF V600E mutation allele to BRAF normal allele was 7% to 30%.

TABLE 4

| Patient | Saliva (Presence or absence of BRAF V600E mutation) | Blood (Presence or absence of BRAF V600E mutation) | BRAF V600E mutation allele percentage in brain tissue (%) |
|---|---|---|---|
| GG221 | — | — | 15.44 |
| GG231 | — | — | 17.86 |
| GG249 | — | — | 19.05 |

Example 3

Confirmation of Cell-Specific Presence of BRAF V600E Mutation Using Laser Capture Cell Lamination A prototype of an appropriate model living organism should be prepared to use for patient treatment, but before preparing the prototype of the model organism, it was required to confirm whether the BRAF V600E mutation was present accurately in a nerve cell, or whether it was present in a glia-based cell line, and therefore the following experiment was conducted.

To confirm whether the BRAF V600E mutation was present accurately in a nerve cell, or whether it was present in a glia-based cell line, after staining tissue of GG221 and GG231 patients in which the BRAF V600E mutation was confirmed with a marker specific to a nerve cell and a marker specific to glia, respectively, using an immunofluorescent staining method, only a specific tissue type of cells were separated using a method called laser capture microscope anatomy to confirm presence or absence of BRAF V600E.

The surgical tissue block in which BRAF V600E mutation was confirmed among ganglioglioma patient tissue used in Example 2 (GG221, GG231 patient tissue) was cultured in newly prepared 4% (w/v) paraformaldehyde under phosphate-buffered (PB) (fixation), 20% (w/v) buffered sucrose (cryoprotect), and 7.5% (w/v) gelatin under 10% (w/v) sucrose/PB overnight to make a gelatin-embedded tissue block, and it was stored at −80° C.

The prepared gelatin-embedded tissue block was rapidly soaked in 2-methylbutanes at −50° C. and the gelatin embedded tissue block was rapidly frozen, and a cryostat-cut section having a thickness of 10 um was made using a cryostat microtome (Leica) under the circumstance of −20° C. or below, and the cryostat-cut section was put on a glass slide, and it was blocked with PBS-GT (0.2% (w/v) gelatin and 0.2% (v/v) Triton X-100 in PBS) at a room temperature for one hour, and it was stained with the following antibodies: mouse monoclonal anti-NeuN (1:200, #MAB377, Millipore) and rabbit polyclonal anti-oligodendrocyte Lineage Transcription Factor 2 (Olig2) (1:500, AB9610, Millipore). After 3 times of PBS cleaning, the tissue slide was stained with the following secondary antibodies: Alexa Fluor 555-conjugated goat antibody to mouse (1:200 dilution; A21422, Invitrogen) or Alexa Fluor 488-conjugated goat antibody to rabbit (1:200 dilution; A11008, Invitrogen). DAPI comprised in a mounting solution (P36931, Life technology) was used for nuclear staining. A fluorescent image was obtained using Leica DMI3000 B inverted microscope. Approximately 50 cells only that were NeuN positive and Olig2 negative, or in contrast, NeuN negative and Olig2 positive were detached using PALM MicroBeam (Carl Zeiss) microscope among stained tissue, and only the genomic DNA was extracted with QIAamp DNA Micro Kit, and then PCR was performed using primers of Table 5, and then the amplified PCR products were purified using MEGAquick spin total fragment purification kit (Intron, Korea), and then Sanger sequencing was performed using BioDye Terminator and automatic sequencer system (Applied Biosystems).

TABLE 5

| Name | Primer | SEQ ID NO |
|---|---|---|
| BRAF_LCM_F | 5'-TGCTTGCTCTGATAGGAAAATG-3' | 5 |
| BRAF_LCM_R | 5'-AGCCTCAATTCTTACCA TCCAC-3' | 6 |

As a result, as could be confirmed in FIG. 2b, it could be confirmed that the BRAF V600E mutation (BRAF Chr7: 140453136 for c.1799T>A mutation) was present in two different kinds of cells that were a nerve cell (left in FIG. 2b) and glia (right in FIG. 2b).

As shown in FIG. 2b, the presence of the same mutation in two different cells, a nerve cell and glia, suggested that the mutation occurred in the common ancestral cells of both nerve cell and glia.

Example 4

Confirmation of Prototypes of Epilepsy Patients in Mice Expressing BRAF V600E Mutation 4-1. Confirmation of Spontaneous Seizures in Animal Model Mice Conditional floxed BRAF V600E mice capable of expressing BRAF V600E mutation shown in epilepsy patients confirmed in Examples 1 to 3 were produced, and the mice were mated with conditional floxed tdTomato mice to produce a timed pregnant of 14 days of embryo, and then a plasmid gene having a Cre recombinase was introduced in uterus by electroporation, and thereby an animal model similar to conditions of ganglioglioma patients.

Specifically, in one example of the present invention, using the known site-directed mutagenesis method, a gene in which the 1910th thymine was substituted to adenine in the sequence disclosed in SEQ ID NO: 4 was amplified, and a product in which this was added to a Cre-dependent LoxP sequence was injected into a mouse embryo, thereby producing a transformed mouse which was substituted by a Cre-dependent condition mutation, and at the 14th day of pregnancy of a mouse obtained by mating the produced mouse and tdTomato mouse (E14), the uterine horn was exposed, and 2 ug/ml of Fast Green (F7252, Sigma, USA) combined to a 2 to 3 ug of plasmid having a Cre recombinase was injected to lateral ventricles of each embryo using a pulled glass capillary. The plasmid having a Cre recombinase (pCAG-Cre-IRES2-GFP, addgene, #26646) was subjected to electroporation by discharging 50V to the head of embryo with an ECM830 eletroporator (BTX-harvard apparatus) which was an electric pulse 5 times of 100 ms at an interval of 900 ms.

Genotyping PCR was conducted using primers of Table 6 and i-Taq TM DNA Polymerase kit (Intron, #25021), by detaching the brain tissue of the mouse embryo electroporated with the plasmid having a Cre recombinase.

TABLE 6

| Name | Primer | SEQ ID NO |
|---|---|---|
| LSL-Braf$^{V600E}$ Fwd | 5'-CCCAGGCTCTTTATGAGAA-3' | 7 |
| LSL-Braf$^{WT}$ Rev | 5'-AGTCAATCATCCACAGAGACCT-3' | 8 |
| LSL-Braf$^{V600E}$ Rev | 5'-GCTTGGCTGGACGTAAACTC-3' | 9 |

As a result, as shown in FIG. 3a, it could be confirmed that the produced mice expressed the BRAF V637E mutant gene (It is mouse BRAF V637E mutation, but it is commonly referred to as BRAF V600E as same as human BRAF V600E, so hereinafter it is described as BRAF V600E).

In order to confirm that the epilepsy wave actually occurred electrophysiologically in the brain of the produced model mice, after a mouse embryo which was electroporated with the plasmid having a Cre recombinase was born, a video-electroencephalography (video-EEG) test was performed from the 3rd week after birth. To analyze the seizure wave with a signal, video electroencephalography surveillance was conducted from the 3rd week after birth. After separating the embryo with its mother, whether a tonic-clonic seizure was started was confirmed by video surveillance for 12 hours a day. Then, the video-electroencephalography for the mice exhibiting a seizure was conducted for 6 hours a day for 2 days or more, thereby investigating the spontaneous seizure exhibiting a seizure wave.

To measure the frequency of the interictal spike and nonspastic brainwave seizure, video electroencephalography data filmed for about 10 to 12 hours were used, and from these data, data of 1 minute were extracted at an interval of 1 hour and were analyzed.

The frequency of the interictal spike and nonspastic brainwave seizure was measured by an observer who did not know the genotype of mice. The interictal spike showed a wave in an epilepsy shape of 200 ms or less at a certain interval and it was defined as the case having an amplitude of 2 times or more than the background brainwave, and the nonspastic brainwave seizure showed at least 2 or more of connected spike-wave (1~4 Hz) with an amplitude of 2 times or more than the background brainwave and it was defined as the case observed in all 4 electrodes.

Specifically, after the mice were weaned (>3 weeks), occurrence of a seizure was confirmed only by video monitoring, and then surgery to implant an electrode to measure electroencephalography was progressed. The electrodes were located on an epidural layer, and A total of 5 electrodes were implanted by implanting 2 in the frontal region (AP+2.8 mm, ML±1.5 mm), 2 in the temporal region (AP-2.4 mm, ML±2.4 mm), and 1 in the cerebellum region, based on the bregma. After the recovery period of 4 days, measurement of electroencephalography for 2-5 days (6 hours a day) per mouse was performed at 6 PM to 2 AM. The electroencephalography signal was amplified by an amplifier (GRASS model 9 EEG/Polysomnograph, GRASS technologies, USA), and the signal was analyzed using pCLAMP program (Molecular Devices, USA) or RHD2000 amplifier, board (Intan technoloties, USA) and MATLAB EEGLAB (http://sccn.ucsd.edu/eeglab).

As a result, as shown in FIG. 3b, 90% or more of mice expressing BRAF V600E mutation showed the spontaneous seizure with the epilepsy wave, and the epilepsy wave showed a high frequency of high amplitude, a spike-wave of high amplitude, and a high frequency of low amplitude. It could be confirmed that the interictal spike was also shown in mice expressing the BRAF V600E mutant gene. The mice showing such a spontaneous seizure showed a systemic tonic-clonic seizure consisting of a tonic phase, a clonic phase and a post-ictal phase, and this was similar to symptoms occurred in ganglioglioma patients. In addition, it was confirmed that the tonic brainwave of the mice showed low-voltage and high-frequency synchronized multi-frequency, and the brainwave of the clonic phase showed a constant form of high-voltage, and the post-ictal phase showed the synchronized damped amplitude. On the other hand, the mice expressing the wildtype BRAF protein did not show a spontaneous seizure or an epilepsy wave.

Thus, based on the above result, it could be seen that a spontaneous seizure with an epilepsy wave occurred in mice in which a plasmid, in which the BRAF V600E mutant gene was inserted, was injected.

4-2. Confirmation of Hyperactivity of Nerve Cells in Animal Model Mice

In order to analyze the epilepsy wave shown in the model mice produced in Example 4-1 electrophysiologically, the experiment was performed by the following method.

Specifically, for the model mice produced in Example 4-1, mouse brain cortex slices were obtained by vibratome and then the spontaneous action potential was measured in artificial cerebrospinal fluid. The composition of the artificial cerebrospinal fluid was as follows: in mM, 124 NaCl, 26 NaHCO3, 3 KCl, 1.25 KH2PO4, 2 CaCl2, 1 MgSO4, and 10 D-glucose. The mouse brain cortex slices were put on a brain multichannel electrode recorder (MED64 probe, #P515A, Panasonic Alpha-Med Sciences), and were supported using a slice anchor kit (SHD-22CKIT, Warner Instruments), and then the artificial cerebrospinal fluid was flowed at a rate of 2 mL/minute for 15 minutes and the epilepsy wave occurring under the condition of 37° C./5% CO2 was measured. Spikes were detected using Mobius software (Alpha Med Scientific).

The result was shown in FIG. 3c and FIG. 4.

According to the left in FIG. 3c, in case of inducing BRAF V600E mutation, an epilepsy seizure occurred in mice close to 90%, and according to the middle in FIG. 3c, in case of mice causing a seizure, they showed an epilepsy prototype from 6 weeks to 7 weeks on average in FIG. 3c.

According to the right in FIG. 3c, the timing of individual seizures of BRAF V600E mutation type of mice could be confirmed.

According to FIG. 4, it was confirmed that synchronized burst firing was shown, in which a spontaneous activity wave and a short period of high amplitude energy were simultaneously emitted on several channels, which was distinctive of epilepsy in brain tissue having BRAF V600E mutation, different from the control group.

Thus, through the above result, it could be confirmed that synchronized burst firing was shown, in which a spontaneous activity wave and a short period of high amplitude energy were simultaneously emitted on several channels, which was distinctive of epilepsy in brain tissue obtained from mice expressing the BRAF V600E mutant protein, different from the brain tissue obtained in mice expressing a wildtype BRAF protein that was the control group. Through this, it could be seen that nerve cells were hyperactivated in the model mice produced in Example 4-1.

Example 5

Confirmation of Epilepsy-Related Tumor Specificity of Mice Expressing BRAF V600E Mutation 5-1 Immunofluorescent Staining of BRAF V600E Mutation Animal Model Mice For the brain tissue of the animal model mice produced in Example 4-1, the experiment was performed by the method as Example 3 to prepare gelatin-embedded tissue block, and it was stored at −80° C.

By the method as Example 3, the gelatin-embedded tissue block was produced as cryostat-cut sections, and they were put on a glass slide, and were stained with the following antibodies: mouse monoclonal anti-NeuN (1:200, #MAB377, Millipore), rabbit polyclonal anti-glial fibrillary acidic protein (GFAP) (1:500, #z0334, DAKO), rabbit polyclonal anti-oligodendrocyte Lineage Transcription Factor 2 (Olig2) (1:500, AB9610, Millipore), rabbit monoclonal anti-S100 beta (1:500, ab52642, Abcam), rabbit monoclonal anti-CD34 (1:500, ab81289, Abcam), mouse monoclonal anti-glutamate decarboxylase 67 (GAD67) (1:500, #MAB5406, Millipore), mouse monoclonal anti-parvalbumin (PV) (1:500, #MAB1572, Millipore), rabbit polyclonal anti-vesicular glutamate transporter 1 (VGLUT1) (1:500, #135 303, Synaptic Systems), rabbit polyclonal anti-vesicular GABA transporter (VGAT) (1:500, #135 002, Synaptic Systems), mouse monoclonal anti-GFP (1:500, #Ab1218, Abcam), rabbit polyclonal anti-GFP (1:500, #Ab290, Abcam), rabbit polyclonal anti-REST (1:200, IHC-00141, Bethyl Laboratories) and rabbit polyclonal anti-CUX1 (1:400, SC13024, Santa cruz). After three times of PBS washing, the tissue slide was stained with secondary antibodies as follows: Alexa 488-conjugated goat anti-rabbit IgG (1:500, #A11008, Invitrogen) or Alexa 555-conjugated goat anti-rabbit IgG (1:500, #21428, Invitrogen). DAPI comprised in a mounting solution (P36931, Life technology) was used for nuclear staining. Images were obtained using Leica DMI3000 B inverted microscope or Zeiss LSM780 confocal microscope. The number of cells which were positive to NeuN was measured using 10× objective lens; 4 to 5 fields were obtained per one subject in the neuron-rich region, and 100 or more cells were recorded per region. The number of DAPI-positive cells represents the total number of cells. The size of neuron cells was measured using an automated counting protocol of ImageJ software (http://rsbweb.nih.gov/ij/) in NeuN positive cells. The circularity and aspect ratio of nerve cells and the angle to the cortex side of dendrites were referenced to values calculated automatically by ImageJ.

5-2. Confirmation of Nerve Cell Dysplasia Through Quantitative Analysis of Immunofluorescent Stained Tissue The result of immunofluorescent staining by the method as Example 5-1 was shown in FIG. 5.

As a result, as could be seen in FIG. 5, it could be confirmed that in case of GFP positive cells of cerebral region in which BRAF V600E mutation was induced by electroporation by the method as Example 4, dysplasia of nerve cells distinctively shown in ganglioglioma was accompanied (A in FIG. 5), and it could be confirmed that in case of the GFP positive cells, the size of cells became bigger and the shape of cells were dented (B in FIG. 5), and the shape of cells and arrangement of branches of nerve cells were arranged in any direction different to normal nerve cells (C in FIG. 5).

5-3. Confirmation of Increases of Glia Proliferation Through Quantitative Analysis of Immunofluorescent Stained Tissue In order to trace daughter cells differentiated from neural progenitor cells having BRAF V600E mutation in animal model mice produced using the method as Example 4-1, mice were obtained by mating transformed mice substituted with a gene expressing BRAD V600E protein dependent to a Cre recombinase with mice capable of producing tdTomato fluorescent protein using the method as Example 4-1, and a Cre recombinase was introduced by electroporation in uterus for the mice, and daughter cells differentiated from neural progenitor cells having BRAF V600E mutation derived from the mice were traced by tdTomato fluorescent staining As a result, as could be seen in FIG. 6b, in the daughter cells differentiated from neural progenitor cells having BRAF V600E mutation, glia-based related astroglia cells (left picture in FIG. 6b) or oligodendroglia (right picture in FIG. 6b) were significantly increased compared to the brain tissue of mice expressing a BRAF normal gene.

To sum up the results of Examples 5-2 and 5-3, it could be seen that the BRAF V600E mutation produced in Example 4 was an animal model which reflected a ganglioglioma disease accompanied with dysplasia of nerve cells and numerical increment of glia well.

5-4. Confirmation of CD34 Marker Through Quantitative Analysis of Immunofluorescent Stained Tissue It was known that ganglioglioma had a characteristic of increased expression of CD34 pathologically in tumor tissue in the past, and therefore the expression of CD34 marker was confirmed by performing immunofluorescent staining by the method as Example 5-1 in the animal model mouse tissue produced by the method as Example 4-1.

As a result, as shown in FIG. 7, it could be confirmed that the expression of CD34 increased 2.2 times even in animal model mouse tissue produced by the method as Example 4-1, different from the control group.

In addition, in order to further confirm characteristics of ganglioglioma, the animal model mouse tissue produced by the method as Example 4-1 was stained using hematoxylin-eosin and DAB immunohistochemical staining used when diagnosing ganglioglioma pathologically.

Specifically, formalin (Sigma, #HT501128) was injected through heart of the animal model mice produced by the method as Example 4-1 and was fixed, and then paraffin was penetrated into a paraffin embedding device (Leica TP1020) over one day to obtain formalin-fixed paraffin-embedded mouse brain tissue. The formalin-fixed paraffin-embedded mouse brain tissue was cut in a thickness of 4 um using microtome (Leica RM 2135), and then general hematoxylin-eosin staining was conducted. For immunohistochemical staining of CD34, at first, antigen collection for slides was performed using sodium citrate, and they were hydrated using a gradual concentration of alcohol, and then the intrinsic peroxidase activity was removed using 3% (w/w) hydrogen peroxide solution ($H_2O_2$) (Sigma aldrich, H6520). Then, the tissue was blocked using a blocking solution, PBS-GT solution (0.2% (w/v) gelatin and 0.2% (v/v) Triton X-100 under PBS), and then it was stored at a room temperature using an anti-CD34 primary antibody (1:500, ab81289, Abcam). After three times of PBS washing and staining with a secondary antibody, antigen-binding sites in tissue were visualized using 3,3'-Diaminobenzidine substrate solution (DAB, Vector Laboratories). To exclude a bias by the image intensity, normal and BRAF V600E mutant mouse tissue was reacted for the same time, and background staining was performed with hematoxylin.

As a result, as shown in the right picture of FIG. 8, it could be confirmed that the expression of CD34 which was not stained in the normal tissue was remarkable in the area where the mutation occurred in the BRAF V600E mutant mouse brain tissue.

To sum up the results of FIG. 7 to FIG. 9, it could be seen that the expression of CD34 was significantly increased in the mouse brain tissue having BRAF V600E somatic genome mutation, compared to the mouse brain tissue having a normal gene, and such a pattern was distinctively shown along with nerve cells and tissue in which the mutation was induced by electroporation in uterus particularly.

5-5. Confirmation of Cortical Dyslamination Through Quantitative Analysis of Immunofluorescent Stained Tissue Since ganglioglioma has been known to accompany local cortical dysplasia or have many cases of observed cortical dyslamination as a part of malformation of cortical development in tumor tissue, in order to confirm whether the similar aspect was shown in the animal model mice produced by the method as Example 4-1, the animal model mouse tissue produced by the method as Example 401 was fixed and prepared by the method as Example 5-4, and then the layer of cortex was classified by the method as Example 5-1, and thereby staining was performed by Cux1 marker which could be confirmed.

As a result, as shown in FIG. 9, it could be confirmed that the Cux1 marker was intensively observed in the bottom part as well as the top part of cortex in the mouse brain tissue having BRAF V600E somatic genome mutation, different from the mouse brain tissue having a normal gene. In particular, it was confirmed that the distribution of nerve cells which were positive to Cux1 had negative correlation statistically significantly in mice having BRAF V600E mutation different from the normal group, and thereby it could be seen that cortical dyslamination of mouse brain tissue having BRAF V600E somatic genome mutation was remarkably shown.

In addition, when the animal model mouse tissue produced by the method as Example 4-1 was under immunohistofluorescent analysis to confirm the distribution of cells which were positive to NeuN and tdTomato concurrently, as could be confirmed in the top of FIG. 10, it could be confirmed that nerve cells which were positive to NeuN and positive to tdTomato were significantly distributed in the layer of the bottom part of cortex in which cells derived from the mouse brain tissue having BRAF V600E mutation were not normally distributed ($r=-0.1122$, $p<0.0001$).

However, by the bottom of FIG. 10, it could be seen that hyperplasia in glia shown in Example 5-3 was not simultaneously transmitted in nerve cells. In other words, only the malposition in cortex was shown without proliferation of cells in nerve cells.

5-6. Result Arrangement "G Summary

Through the results of Examples 5-2, 5-3, 5-4 and 5-5, it could be confirmed that the animal model mouse tissue produced by the method as Example 4-1 reflected opinions of tumors with high frequency of accompanying epilepsy among pediatric low grade glioma including ganglioglioma. The above opinions include dysplasia of nerve cells, glia hyperplasia, abnormality of arrangement of dendrites of nerve cells, CD34-positive opinion and transmission of cortical dyslamination, by BRAF V600E mutation, and the like.

Example 6

Phenotypes According to Spatial Acquisition of BRAF V600E Mutation

In case of pediatric epilepsy-related tumor and pediatric low grade glioma and the animal model mice suggested in the present invention examined in Examples 3 and 5-2, the BRAF V600E mutation was present in glia, and therefore it is required to confirm which mutation plays an important role in inducing epilepsy among mutations derived from nerve cells or glia.

For this, a mouse capable of expressing the BRAF V600E mutation found in ganglioglioma patients in a Cre-dependent manner was produced by a similar method to Example 4-1, and a plasmid having a Cre recombinase at the 1th day after the mouse birth was electroporated, and then behavior was monitored for about 90 days.

Specifically, in the differentiation of cortical nervous system, the differentiation of nerve cells and glia were actively proceeded at E14 and after birth, respectively, and therefore, when a Cre plasmid was injected at the 14th day of pregnancy of the mother mouse who was in pregnancy of an embryo capable of expressing a Cre-dependent gene, the mutation occurred in nerve cells and glia, and when a Cre plasmid was injected at the first day after birth of the mouse, the mutation occurred in glia, so in order to generate BRAF V600E mutation only in glia using the above fact, mice were produced as Example 4-1, but a Cre plasmid was injected at the first day after birth of the mouse capable of expressing a Cre-dependent gene.

As a result, as shown in B of FIG. 11, it could be confirmed that a seizure did not occur at all in the mouse produced so as to generate BRAF V600E mutation only in glia (GFAP, and OLIG2 were glia-confirming markers).

In addition, in order to confirm whether glia hyperplasia was caused in the mouse produced so as to generate BRAF V600E mutation only in glia, the experiment was performed as Example 5-3, and as a result, as shown in C of FIG. 11, it could be confirmed that glia hyperplasia was significantly shown continuously.

Thus, to sum up the results, it could be seen that the development of epilepsy by BRAF V600E somatic genome mutation was independent of the mutation originated from glia and BRAF V600E mutant generated in nerve cells played an important role in an epilepsy pathogenic mechanism, and in addition, it could be seen that proliferation of a benign tumor in which BRAF V600E mutation occurred only in glia increased.

Example 7

Phenotypes According to Temporal Acquisition of BRAF V600E Mutation

Since epilepsy-related tumor was found with a high ratio in children, whether there was a phenotypic difference between acquisition of BRAF V600E mutation of childhood and acquisition of the mutation in adult mice in the mouse model of the present invention such as epidemiological information of patients was confirmed by the following method.

7-1. BRAF V600E Mutation Inducible Using Tamoxifen in Adult Mice

In order to change time of occurrence of BRAF V600E mutation in the animal model mouse, the following method was used.

Timed pregnant of conditional floxed BRAF V600E mice was made by the method as Example 4-1, and a plasmid gene having a tamoxifen inducible Cre recombinase was introduced in uterus, and then from the 30th day after birth, tamoxifen was intraperitoneally injected to induce the BRAF V600E somatic genome mutation in model mouse brain appropriately. Tamoxifen was treated from the 30th day after birth, and behavior of mice was monitored for about 30 days.

Specifically, for introduction of genome in uterus, the uterine horn was exposed of timed pregnant 14th day (E14), and 2 ug/ml of Fast Green (F7252, Sigma, USA) combined to a 2 to 3 ug of plasmid having a Cre recombinase was injected to lateral ventricles of each embryo using a pulled glass capillary. The plasmid was subjected to electroporation by discharging 50V to the head of embryo with an ECM830 eletroporator (BTX-harvard apparatus) which was an electric pulse 5 times of 100 ms at an interval of 900 ms. In addition, tamoxifen (Sigma, T5648) was shaded in corn oil (Sigma, C8267) at a concentration of 10 mg/ml at 37° C. for 1 day to store, and 100 ug/g tamoxifen was intraperitoneally injected for both normal mice and mutant mice, and it was treated once a day for 5 consecutive days, and after the withdrawal period for immediately next one week, it was treated again for 5 consecutive days. After treatment of tamoxifen, behavior observation for mice was started, and behavior was compared using a mouse treated with only corn oil without tamoxifen or a normal mouse treated with tamoxifen as a control group. A schematic flow of the above experimental procedure was shown in FIG. 12.

As a result, as could be confirmed in the right graph in FIG. 12, in case that the BRAF V600E mutation was induced in nerve cells of adult mice of after 30 days after birth, mice did not exhibit icta seizures.

7-2. BRAF V600E Mutation Adult Mice Using a Virus

In order to change time of occurrence of BRAF V600E mutation in the animal model mice, BRAF V600E mutation adult mice were produced using a virus by the following method.

Specifically, mice after 30 days after birth were anesthetized, and heads were fixed in a stereotactic surgery device (Stoelting Co., Wood Dale, IL) and a hole having a diameter of about 1 mm was made in a brain bone with a dental drill. 0.5 uL AAV9.CamKII.HI.eGFP-Cre.WPRE.SV40 (Penn Vector Core Philadelphia, PA; titer 6.54×1013 GCml−1) was injected into somatosensory cortex (AP: −0.5; ML: −2.0~− 2.5; DV: −0.5) using a glass micropipette at a slow rate (1 nL per sec). In 2 weeks, behavior of mice in which a virus was injected was observed and measurement of brainwaves was started. After observation was finished, frozen tissue slides of brain were prepared in a thickness of 20 um with paraformaldehyde by the method as Example 5-1, and they were observed with a microscope, and whether fluorescent reporter protein injected through the virus expressed well was re-confirmed.

As a result, as could be confirmed in FIG. 13, as same as inducement of BRAF V600E mutation in adult mice using tamoxifen in Example 7-1, a seizure was not shown also in mice in which the mutation was induced using a virus.

7-3. Confirmation of a Cytologically Abnormal Aspect by BRAF V600E Mutation Induction in Adult Mice After inducing the BRAF V600E somatic genome mutation in adult mice as the method of Examples 7-2 and 7-3, dysplasia of nerve cells was confirmed by the method as Example 5-2.

As a result, as could be confirmed in FIG. 14, in case of inducing (BRAFWT/LSL-V600E) the BRAF V600E mutation in adult mice, as same as the BRAF V600E mutant mouse produced by the method as Example 4-1, compared to the mouse having a normal BRAF gene (BRAFWT/WT), there was no big difference in the size of cells (A in FIG. 14), circularity and aspect ratio of cells (B in FIG. 14) and the angle to the cortical surface of dendrites (C in FIG. 14) and the like from the mouse having a normal BRAF gene (absence of dysplasia of nerve cells).

In addition, in case of inducing the BRAF V600E mutation in adult mice using tamoxifen, compared to the mouse having a normal BRAF gene, there was no big difference in the size of cells, the circularity and aspect ratio of cells, and the angle to the cortical surface of dendrites and the like from the mouse having a normal BRAF gene (D in FIG. 14) (absence of dysplasia of nerve cells).

Through the above result, it could be seen that when the BRAF V600E mutation occurred only in nerve cells at an embryonic development stage, dysplasia of nerve cells was induced and thereby epilepsy was caused.

Example 8

Confirmation of Reduction of Seizures by Injection of a BRAF V600E Specific Inhibitor In order to reduce the frequency of seizures generated in BRAF V600E mutant mice produced by the method as Example 4-1, a BRAF V600E specific inhibitor was treated and its effect was confirmed.

Specifically, a BRAF V600E mutant protein-specific activity inhibitor (Vemurafenib) was injected into brain tissue of BRAF V600E mutant mice produced by the method as Example 4-1 for a long period. They were generally anesthetized by peritoneal injection of a solution in which Zoletil (0.01 mg/kg) and rompun (0.2 mg/kg) were mixed, and vehicle (50% (v/v) DMSO in DW) or 500 um PLX4032 (Vemurafenib) (V-2800, LC laboratories) was under chronic intracranioventricular injection (cICV) into right ventricle space (AP: −0.6; ML: −1.0; DV: −2.0) in an osmotic pump (ALZET pumps 2004 or 2006, ALZET Osmotic Pumps, Cupertino, CA) with infusion cannula (ALZET brain infusion kit 3). In order to trace brainwaves, after inserting 4 EEG probes (left/right frontal lobes and left temporal lobes, cerebellum as a reference) into the animal model mouse head by the method as Example 4-1, brainwave signals were obtained, and 5-6 weeks later, mice were sacrificed and brain was removed to use for the further research, and then whether the semipermeable membrane in the osmotic pump was reduced was re-confirmed. Drug injection was conducted by 4 weeks ~6 weeks, and at that time, the brainwaves of mice were monitored and recorded.

The result was shown in FIG. 15 to FIG. 17.

According to FIG. 15, it could be confirmed that icta seizures were reduced about 4 times in case of mice in which the BRAF V600E specific inhibitor was injected (FIG. 15 B), and it could be electrophysiologically confirmed that seizures were continuously reduced when treating the BRAF V600E specific inhibitor for 6 weeks (FIG. 15 C).

According to FIG. 16, it could be confirmed that the electrographic seizures were reduced 2 times to 3 times (middle in FIG. 16), and the interictal spikes were reduced 1.3 times to 1.5 times.

In addition, according to FIG. 17, it could be confirmed that the seizure frequency was not reduced in case of acute intracerebroventricular injection (3 times/day, 5 uL injection for 8 minutes) (left in FIG. 17) or oral administration (PO, per oral) (right in FIG. 17) of the BRAF V600E specific inhibitor.

Example 9

Seizure-Related Mechanism by BRAF V600E Mutation

The abnormal activity of the mTOR signaling pathway has been known to induce an epileptic seizure, and the BRAF V600E mutation has been known to activate the MARK signaling pathway of Ras-Raf-MEK-ERK. On the other hand, the MAPK signaling pathway of Ras-Raf-MEK-ERK known to be activated by the BRAF V600E mutation has been known to activate the mTOR signaling pathway by crosstalk with the mTOR signaling pathway, and it has been reported that the expression of mTOR signaling pathway-related proteins was increased in tissue of ganglioglioma patients. Thus, in order to confirm whether an epilepsy seizure was caused by activation of the mTOR signaling pathway by the BRAF V600E mutation, the following experiment was performed.

Specifically, for the animal model mice produced by the method as Example 4-1, rapamycin which was an mTOR-specific inhibitor was intraperitoneally injected, and then the change was confirmed. Rapamycin (LC Labs, USA) was diluted by 20 mg/ml in 100% ethanol to prepare a stock solution, and then was stored at 20° C. Before injecting rapamycin to the animal model mice, the rapamycin stock solution was diluted in 5% (w/v) polyethylene glycol 400 and 5% (v/v) Tween80 to prepare a solution of 1 mg/mL rapamycin and 4% (v/v) ethanol. The prepared solution was administered by intraperitoneal injection at a concentration of 1 to 10 mg/kg for 2 weeks (10 mg/kg/d intraperitoneal injection, for 2 weeks).

As a result, as shown in FIG. 18, despite of administration of rapamycin, the frequency of epilepsy seizures of BRAF V600E animal model mice did not decrease, and the BRAF V600E mutation animal model mouse tissue did not show a big difference compared to the normal mouse tissue in phosphorylation of S6 protein in the mTOR subpath.

The invention claimed is:

1. A murine model with ganglioglioma or epilepsy caused by ganglioglioma, wherein the animal model is prepared by obtaining an embryo from a conditional mutant transgenic animal including a nucleic acid molecule encoding a BRAF mutant protein and inducing expression of the BRAF mutant protein or the nucleic acid molecule encoding the BRAF mutant protein in neural progenitor cells of lateral ventricle of the embryo at embryonic day 14 (E14), wherein the BRAF mutant protein consisting of an amino acid sequence comprising a mutation in which valine at position 600 is substituted to glutamic acid in an amino acid sequence of SEQ ID NO: 1, or a BRAF mutant protein consisting of an amino acid sequence comprising a mutation in which valine at position 637 is substituted to glutamic acid in an amino acid sequence of SEQ ID NO: 3, and wherein the animal model has characteristics of activated MARK signaling pathway of Ras-Raf-MEK-ERK, dysplasia of nerve cells, and malformation of cortical development.

2. The murine model according to claim 1, wherein the animal has a spontaneous seizure.

3. The murine model according to the claim 1, wherein the mutant nucleic acid molecule comprises a mutation in which thymine at position 1799 is substituted to adenine in the nucleotide sequence of SEQ ID NO: 2, or thymine at position 1910 is substituted to adenine in the nucleotide sequence of SEQ ID NO: 4.

4. The murine model according to the claim 1, wherein the ganglioglioma or epilepsy caused by ganglioglioma is not caused by activation of the mTOR signaling pathway.

5. The murine model according to claim 1, wherein the animal model expresses the BRAF mutant protein in nerve cells and glial cells of brain.

* * * * *

SEQUENCE LISTING

<160> NUMBER OF SEQ ID NOS: 9

<210> SEQ ID NO 1
<211> LENGTH: 766
<212> TYPE: PRT
<213> ORGANISM: Homo sapiens

<400> SEQUENCE: 1

```
Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220
```

-continued

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
            245                 250                 255

Gln Gly Phe Arg Cys Gln Thr Cys Gly Tyr Lys Phe His Gln Arg Cys
        260                 265                 270

Ser Thr Glu Val Pro Leu Met Cys Val Asn Tyr Asp Gln Leu Asp Leu
    275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
            325                 330                 335

Ser Lys Ser Ile Pro Ile Pro Gln Pro Phe Arg Pro Ala Asp Glu Asp
        340                 345                 350

His Arg Asn Gln Phe Gly Gln Arg Asp Arg Ser Ser Ala Pro Asn
    355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
            405                 410                 415

Gln Lys Ser Pro Gly Pro Gln Arg Glu Arg Lys Ser Ser Ser Ser Ser
        420                 425                 430

Glu Asp Arg Asn Arg Met Lys Thr Leu Gly Arg Arg Asp Ser Ser Asp
    435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
            485                 490                 495

Ala Phe Lys Asn Glu Val Gly Val Leu Arg Lys Thr Arg His Val Asn
        500                 505                 510

Ile Leu Leu Phe Met Gly Tyr Ser Thr Lys Pro Gln Leu Ala Ile Val
    515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Val Lys Ser Arg Trp Ser Gly Ser His
    595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr

|  | 645 |  | 650 |  | 655 |  |
|---|---|---|---|---|---|---|

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
        690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 2
<211> LENGTH: 2949
<212> TYPE: DNA
<213> ORGANISM: Homo sapiens

<400> SEQUENCE: 2

```
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgatttttc tgtttctagc tctgcatcaa tggataccgt     420
tacatcttct tcctcttcta gcctttcagt gctaccttca tctctttcag ttttttcaaaa    480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga     720
agaattgcat gtggaagtgt tggagaatgt tccacttaca acacacaact ttgtacgaaa     780
aacgtttttc accttagcat tttgtgactt ttgtcgaaag ctgcttttcc agggtttccg     840
ctgtcaaaca tgtggttata aatttcacca gcgttgtagt acagaagttc cactgatgtg     900
tgttaattat gaccaacttg atttgctgtt tgtctccaag ttctttgaac caacccaat      960
accacaggaa gaggcgtcct tagcagagac tgccctaaca tctggatcat cccttccgc    1020
acccgcctcg gactctattg ggccccaaat tctcaccagt ccgtctcctt caaaatccat   1080
tccaattcca cagcccttcc gaccagcaga tgaagatcat cgaaatcaat tgggcaacg    1140
agaccgatcc tcatcagctc ccaatgtgca tataaacaca atagaacctg tcaatattga   1200
tgacttgatt agagaccaag gatttcgtgg tgatggagga tcaaccacag tttgtctgc    1260
taccccccct gcctcattac ctggctcact aactaacgtg aaagcctta agaaatctcc     1320
aggacctcag cgagaaagga agtcatcttc atcctcagaa acaggaatc gaatgaaaac    1380
acttggtaga cgggactcga gtgatgattg ggagattcct gatgggcaga ttacagtggg   1440
```

-continued

```
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca tttttgtggat   1920 ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct tcccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggggata   2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaatgtgg atgtcttttta tttccttgaa gcaataaact aagtttcttt    2940
ttataaaaa                                                            2949
```

<210> SEQ ID NO 3
<211> LENGTH: 804
<212> TYPE: PRT
<213> ORGANISM: Mus musculus

<400> SEQUENCE: 3

```
Met Ala Ala Leu Ser Gly Gly Gly Ser Ser Gly Gly Gly Gly
1               5                   10                  15

Gly Gly Gly Gly Gly Gly Gly Gly Asp Gly Gly Gly Ala Glu
                20                  25                  30

Gln Gly Gln Ala Leu Phe Asn Gly Asp Met Glu Pro Glu Ala Gly Ala
            35                  40                  45

Gly Ala Ala Ala Ser Ser Ala Ala Asp Pro Ala Ile Pro Glu Glu Val
        50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
```

```
                100              105                110
Glu Gln Gln Leu Leu Glu Ser Leu Val Phe Gln Thr Pro Thr Asp Ala
            115                 120                 125

Ser Arg Asn Asn Pro Lys Ser Pro Gln Lys Pro Ile Val Arg Val Phe
            130                 135             140

Leu Pro Asn Lys Gln Arg Thr Val Val Pro Ala Arg Cys Gly Val Thr
145                     150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
            195                 200                 205

Glu Val Leu Glu Asn Val Pro Leu Thr Thr His Asn Phe Val Arg Lys
            210                 215                 220

Thr Phe Phe Thr Leu Ala Phe Cys Asp Phe Cys Arg Lys Leu Leu Phe
225                     230                 235                 240

Gln Gly Phe Arg Cys Gln Thr Cys Gly Tyr Lys Phe His Gln Arg Cys
                    245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
                275                 280                 285

Ala Ser Phe Pro Glu Thr Ala Leu Pro Ser Gly Ser Ser Ser Ala Pro
            290                 295                 300

Pro Ser Asp Ser Thr Gly Pro Gln Ile Leu Thr Ser Pro Ser Pro Ser
305                     310                 315                 320

Lys Ser Ile Pro Ile Pro Gln Pro Phe Arg Pro Ala Asp Glu Asp His
                    325                 330                 335

Arg Asn Gln Phe Gly Gln Arg Asp Arg Ser Ser Ser Ala Pro Asn Val
                340                 345                 350

His Ile Asn Thr Ile Glu Pro Val Asn Ile Asp Glu Lys Phe Pro Glu
            355                 360                 365

Val Glu Leu Gln Asp Gln Arg Asp Leu Ile Arg Asp Gln Gly Phe Arg
            370                 375                 380

Gly Asp Gly Ala Pro Leu Asn Gln Leu Met Arg Cys Leu Arg Lys Tyr
385                     390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
                420                 425                 430

Leu Ser Ala Thr Pro Pro Ala Ser Leu Pro Gly Ser Leu Thr Asn Val
                435                 440                 445

Lys Ala Leu Gln Lys Ser Pro Gly Pro Gln Arg Glu Arg Lys Ser Ser
            450                 455                 460

Ser Ser Ser Ser Ser Glu Asp Arg Ser Arg Met Lys Thr Leu Gly Arg
465                     470                 475                 480

Arg Asp Ser Ser Asp Asp Trp Glu Ile Pro Asp Gly Gln Ile Thr Val
                    485                 490                 495

Gly Gln Arg Ile Gly Ser Gly Ser Phe Gly Thr Val Tyr Lys Gly Lys
                500                 505                 510

Trp His Gly Asp Val Ala Val Lys Met Leu Asn Val Thr Ala Pro Thr
            515                 520                 525
```

```
Pro Gln Gln Leu Gln Ala Phe Lys Asn Glu Val Gly Val Leu Arg Lys
        530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys

<210> SEQ ID NO 4
<211> LENGTH: 9728
<212> TYPE: DNA
<213> ORGANISM: Mus musculus

<400> SEQUENCE: 4
ccctcaggct cggctgcgcc ggggccgccg gcgggttcca gaggtggcct ccgccccggc    60
cgctccgccc acgccccccg cgcctccgcg cccgcctccg cccgccctgc gcctcccttc   120
cccctccccg ccccgcggcg gccgctcggc ccggctcgcg cttcgaagat ggcggcgctg   180
agtggcggcg gtggcagcag cagcggtggc ggcggcggcg gtgcggcgg cggtggcggt   240 ggcgacggcg gcgcggcgc cgagcagggc caggctctgt tcaatggcga catggagccg   300
gaggccggcg ctggcgccgc ggcctcttcg gctgcggacc cggccattcc tgaagaggta   360
tggaatatca agcaaatgat taagttgaca caggaacata tagaggccct attgacaaa   420 tttggtggag agcataaccc accatcaata tacctggagg cctatgaaga gtacaccagc   480
aagctagatg cccttcagca aagagaacag cagcttttgg aatccctggt ttttcaaact   540
```

```
cccacagatg catcacggaa caaccccaag tcaccacaga aacctatcgt tagagtcttc    600
ctgcccaaca aacagaggac agtggtaccc gcaagatgtg gtgttacagt tcgagacagt    660
ctaaagaaag cactgatgat gagaggtctc atcccagaat gctgtgctgt ttacagaatt    720
caggatggag agaagaaacc aattggctgg gacacggaca tttcctggct tactggagag    780
gagttacatg ttgaagtact ggagaatgtc ccacttacaa cacacaactt tgtacggaaa    840
acttttttca ccttagcatt ttgtgacttt tgccgaaagc tgcttttcca gggtttccgt    900
tgtcaaacat gtggttataa atttcaccag cgttgtagta cagaggttcc actgatgtgt    960
gtaaattatg accaacttga tttgctgttt gtctccaagt tctttgagca tcacccagta   1020
ccacaggagg aggcctcctt cccagagact gcccttccat ctggatcctc ttccgcaccc   1080
ccctcagact ctactgggcc ccaaatcctc accagtccat ctccttcaaa atccattcca   1140
attccacagc ccttccgacc agcagatgaa gatcatcgca atcagtttgg gcaacgagac   1200
cggtcctcct cagctcccaa tgttcatata aacacaattg agcctgtgaa tatcgatgaa   1260
aaattcccag aagtggaatt acaggatcaa agggatttga ttagagacca ggggtttcgt   1320
ggtgatggag cccccttgaa ccaactgatg cgctgtcttc ggaaatacca atcccggact   1380
cccagccccc tcctccattc tgtccccagt gaaatagtgt ttgattttga gcctggccca   1440
gtgttcagag ggtcaaccac aggcttgtcc gccaccccgc ctgcctcatt acctggctca   1500
ctcactaacg tgaaagcctt acagaaatct ccaggtcctc agcgggaaag gaagtcatct   1560
tcttcctcat cctcggagga cagaagtcgg atgaaaacac ttggtagaag agattcaagt   1620
gatgactggg agattcctga tggacagatt acagtgggac agagaattgg atctgggtca   1680
tttggaactg tctacaaggg aaagtggcat ggtgatgtgg cagtgaaaat gttgaatgtg   1740
acagcaccca cacctcaaca gctacaggcc ttcaaaaatg aagtaggagt gctcaggaaa   1800
actcgacatg tgaatatcct ccttttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga aatctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca aacatcaaca caagggatca gataattttt   2280
atggtgggac gaggatacct atctccagat ctcagtaagg tacggagtaa ctgtccaaaa   2340
gccatgaaga gattaatggc agagtgcctc aaaaagaaaa gagacgagag accactcttt   2400
ccccaaattc tcgcctccat tgagctgctg gcccgctcat tgccaaaaat tcaccgcagt   2460
gcatcagaac cttccttgaa tcgggctggt ttccaaacag aagattttag tctgtatgct   2520
tgtgcttctc cgaaaacacc catccaagca gggggatatg gagaatttgc agccttcaag   2580
tagccagtcc atcatggcag catctactct ttatttctta agtcttgtgt tcatacagtt   2640
tgttaacatc aaaacacagt tctgttcctc aaaaaatttt ttaaagatac aaaattttca   2700
atgcataagt tcatgtggaa cagaatggaa tttcctattc aacaaagag ggaagaatgt    2760
tttaggaacc agaattctct gctgcccgtg tttcttcttc aacataacta tcacgtgcat   2820
acaagtctgc ccattcccaa gaagaaagag gagagaccct gaattctgcc cttttggtgg   2880
```

```
tcaggcatga tggaaagaat tgctgctgc  agcttgggaa aattgctatg gaaagtctgc  2940
cagtcgactt tgcccttcta accaccagat cagcctgtgg ctggtcatct gatggggcga  3000
tttccatcac caagcatcgt tcttgcctat tctgggatta tgttgtggag cactttccct  3060
gtccagcacc gttcatttct gagggatgga gtaaatgcag cattcccttg tgtagcgcct  3120
gttcagtcct cagcagctgc tgtcacagcg aagctttta  cagttaagtg gtggggaga   3180 gttgaggaga gcctgcctcg gggcagagaa aaggggggtgc tgcatcttct tcctcacctc  3240
cagctctctc acctcgggtt gccttgctca ctgggctccg cctaaccact caggctgctc  3300
agtgctggca cacattgcct tctttttctca ttgggtccag caattgagga gagggttggg  3360
ggattgtttc ctcctcaatg tagcaaattc tcaggaaaat acagtccata tcttcctctc  3420
agctcttcca gtcaccaaat acttacgtgg ctcctttgtc caggacataa acaccgtgg   3480 acaacaccta attaaaagcc tacaaaactg cttactgaca gttttgaatg tgagacactt  3540
gtgtaattta aatgtaaggt acaggtttta atttctgagt ttcttctatt tttatttaaa  3600
agaagaaaat aattttcagt tttaattgga ataaatgagt acttcccaca agactatata  3660
ccctgaaaat tatatttttg ttaattgtaa acaacttta  aagaataatt attatccttt  3720
tctctaccta aaaattatgg ggaatcttag cataatgaca attatttata cttttaaat   3780 aaatggtact tgctggatcc acactaacat cttttgctaac aatcccattg tttcttccaa  3840
cttaactcct acactacatc ctacatcctc tttctagtct tttatctata atatgcaacc  3900
taaaataaac gtggtggcgt ctccattcat tctccctctt cctgttttcc ccaagcctgg  3960
tcttcaaaag gttgggtaat cggtccctga gctccctagc tggcaatgca actattaggg  4020
acattggagt tgcaggagag caggaagcct gtccccagct gttcttctag aaccctaaat  4080
cttatctttg cacagatcaa aagtatcacc tcgtcacagt tctccttagc ctttacttac  4140
aggtaatata aataaaaatc accatagtag taaagaaaac aactggatgg attgatgacc  4200
agtacctctc agagccagga atcttgaatc tccaggattt atacgtgcaa atttaaggag  4260
atgtacttag caacttcaag ccaagaactt ccaaaatact agcgaatcta aaataaaatg  4320 gaatttgag  ttattttaa  agttcaaatt ataattgata ccactatgta tttaagccta   4380
ctcacagcaa gttagatgga ttttgctaaa ctcattgcca gactgtggtg gtggtggtgg  4440
tagtgtgcac ctttaatcca agcaactcag caatcagaat gaggtaaatc tctgtgaata  4500
caaggcctgc ctagtctgca gcgctagttc caggatagcc agggctacac acacaaaaac  4560
cctctctcaa aaaaacaaa  attaattagt tgataataaa aataactaa  agtatcatca  4620 aaggaaggcc tactggaagt tttatatatt cccagtaaat tgaaaatat  tctgaagtta  4680 ttaaccagtt agcaacaatg tgttttaag  tcttacataa acagagcaaa gtcttcaaat  4740
gtttcagagc tgagaagata attgtgcttg atatgaaaaa tagcctctcc atatgatgtg  4800
ccacattgaa aggcgtcatt acccttttaa atacttctta atgtggcttt gttccctta   4860 cccaggatta gctagaaaga gctaggtagg cttcggccac agttgcacat ttcgggcctg  4920
ctgaagaatg ggagctttga aggctggcct tggtggagga gcccctcagt gctggagggt  4980
ggggcgtgta cgcagcatgg aagtggtcta gacagagtgc aaagggacag acttcttttct  5040 cattttagta tagggtgatg tctcacttga aatgagaaag tagagttgat attaaacgaa  5100
gctgtgccca gaaccaggc  tcagggtatt gtgagatttt cttttaaat  agagaatata  5160 aaagatagaa ataatatttt aaaccttcct tcttattttc tatcaaatag atttttttta  5220
tcatttgcaa acaacataaa aaaaggtttc ttttgtgggg ttttcttttcc ttctttttttt 5280
```

```
tttttttttt tttttaagac tgcagataat cttgttgagc tcctcggaaa atacaaggaa    5340
gtccgtgttt gtgcagagcg ctttatgagt aactgtatag acagtgtggc tgcttcactc    5400
atcccagagg gctgcagctg tcggcccatg aagtggctgc agtgcctcgt gagatctgct    5460
ttgttttgtt tggagtgaag tctttgaaag gtttgagtgc aactatatag gactgttttt    5520
aaataagtag tattcctcat gaactttctc attgttaagc tacaggaccc aaactctacc    5580
actaagatat tattaacctc aaaatgtagt ttatagaagg aatttgcaaa tagaatatcc    5640
agttcgtact tatatgcatc ttcaacaaag attctctgtg acttgttgga tttggttcct    5700
gaacagccca tttctgtatt tgaggttagg agggcataat gaggcatcct aaaagacaat    5760
ctgatataaa ctgtatgcta gatgtatgct ggtaggggag aaagcattct gtaaagacat    5820
gatttaagac ttcagctctg tcaaccagaa accttgtaaa tacttcctgt cttggtgcag    5880
ccccgcccct ttgatcacac gatgttgtct tgtgcttgtc agacactgtc agagctgctg    5940
ttcgtccctc tgcagatctc acctgtcccc actgcacacc cacctcctgc ctcttgcaga    6000
cctcagcatc tagctttagt tggaaacagt tcagggttca ggtgacttct taaaaaaaaa    6060 aaaaaacccct acctcctcag aatgaggtaa tgaatagtta tttatttaaa gtatgaagag    6120
tcaggagcgc tcgaacatga aggtgattta agatggttcc tttcgtgtgt attgtagctg    6180
agcacttgtt tttgtcctaa agggcattat acatttaagc agtgattctg tttaaagatg    6240
ttttctttta aaggtgtagc tcagagtatc tgttgttgga attggtgcca gagtctgctt    6300
aatagatttc agaatcctaa gcttaagtca gtcgcatgaa gttaagtagt tatggtaaca    6360 cttgtgctagc catgatataa ttctactttt taggagtagg tttggcaaaa ctgtatgcct    6420
tcaaagtgag ttggccacag ctttgtcaca tgcacagata ctcatctgaa gagactgccc    6480
agctaagagg gcggaaggat acccttttt cctacgattc gcttctttgt ccacgttggc    6540
attgttagta ctagtttatc agcaccttga ccagcagatg tcaaccaata agctatttt    6600 aaaaccatag ccagagatgg agaggtcact gtgagtagaa acagcaggac gcttacagga    6660
gtgaaatggt gtagggaggc tctagaaaaa tatcttgaca atttgccaaa tgatcttact    6720
gtgccttcat gatgcaataa aaaagctaac attttagcag aaatcagtga tttacgaaga    6780
gagtggccag tctggtttaa ctcagctggg ataatatttt tagagtgcaa tttagactgc    6840
gaagataaat gcactaaaga gtttatagcc aattcacatt tgaaaaataa gaaaatggta    6900
aattttcagt gaaatatttt tttaaagcac ataatcccta gtgtagccag aaatatttac    6960
cacatagagc agctaggctg agatacagtc cagtgacatt tctagagaaa ccttttctac    7020
tcccacgggc tcctcaaagc atggaaattt tatacaaaat gtttgacatt ttaagatact    7080
gctgtagttt agttttgaaa tagtatgtgc tgagcagcaa tcatgtacta actcagagag    7140
agaaaacaac aacaaattgt gcatctgatt tgttttcaga gaaatgctgc caacttagat    7200
actgagttct cagagcttca agtgtaaact tgcctcccaa gtcctgtttg caaatgaagt    7260
tggctagtgc tactgactgc tccagcacat gatggaaggc agggggctgt ctctgaagtg    7320
tcttctataa agggacaata gaatagtgag agacctggtc agtgtgtgtc agctggacac    7380
tccatgctat gggacttgca tcttctgtcc tcaccatccc caagacattg tgctttcctc    7440
agttgtcctc tagctgtttc actcagacac caagatgaat tactgatgcc agaaggggcc    7500
aaaatggcca gtgtgttttg ggggttgtat cagttgactg gacaataact ttaatagttt    7560
cagatcattt attttactt ccattttgac agacatttaa atggaaattt agtcctaact    7620
```

```
tttgtcattt gaaaggaaaa attaacagtt cctataagat acttttgagg tggaatctga    7680
catcctaatt ttttttcttt tcagtgggtt tgcagcgagg gtcttgtatg cactaggcaa    7740
gggttctacc actaagccac atttcccagg aaataaaatg ttaacagtta aaacatacac    7800
acaaatacac aaacacctta ttaccacttt agtaaagtga gagatgtgcg tcctttgtct    7860
cagtctccac gatttcagct gccccttgta tgaataactc agtctcgcta aactgtttac    7920
ttttatttac ctggtttgac tagttgcagc tatataacca gttgtgcatg aggacaacag    7980
ccagtgtgtt tgttttgttt ttggtttttt gtggtacatt ttttgtaaag aattctgtag    8040
attgaagtgc tctttgaaaa cagaactgag atatatttat tcttgttagc atcaaaaaac    8100
attttgtgca aatgatttgc ttttcctggc aggctgagta ccatatccag cgcccacaat    8160
tgcgggttcc catctaccat gtccacaggg gagacagacg ggaagcacat gaggggtgtg    8220
tttacagagt tgtaggagtt atgtagttct cttgttgcct tggaaatcac tgttgtttta    8280
agactgttga acccgtgtgt ttggctgggc tgtgagttac atgaagaaac tgcaaactag    8340
catatgcaga caaagctcac agactaggcg taaatggagg aaaatggacc aaaataaggc    8400
agggtgacac ataaaccttg ggcttcggag aaaactaagg gtggagatga actataatca    8460
cctgaataca atgtaagagt gcaataagtg tgcttattct aagctgtgaa cttcttttaa    8520
atcattcctt tctaatacat ttatgtatgt tccattgctg actaaaacca gctatgagaa    8580
catatgcctt tttattcatg ttaactacca gtttaagtgg ctaaccttaa tgtcttattt    8640
atcttcattt tgtattagtt tacataccag gtatgtgtgt gtgctgtact cttcttccct    8700
ttatttgaaa acacttttca ctgggtcatc tccttggcca ttccacaaca caactttggt    8760
ttggctttca atgtcacctt atttgatggc ctgtgtccca gtagcagaat ttatggtatt    8820
cccattgctg gctgctcttc cgacccttag cttctacagc acttgtctct cctaagatag    8880
tcagaaacta actgatcagg ggatggactt caccattcat cgtgtctctt caattctatt    8940
aaatagacca ctcttgggct ttagaccagg aaaaaggaga cagctctagc catctaccaa    9000
gcctcaccct aaaaggtcac ccgtacttct tggtctgagg acaagtctcc actccagtaa    9060
gggagagggg aggaaatgct tcctgtttga aatgcagtga attcctatgg ctcctgtttc    9120
accacccgca cctatggcaa cccatataca ttcctcttgt ctgtaactgc caaaggttgg    9180
gtttatgtca cttcagttcc actcaagcat tgaaaaggtt ctcatggagt ctgggtgtg     9240
cccagtgaaa agatggggac ttttcatta ccacagacc tctctatacc tgctttgcaa      9300
aaattataat ggagtaacta ttttaaagc ttattttca attcataaga aaagacatt       9360
tattttcaat caaatggatg atgtctctta tcccttatcc ctcaatgttt gcttgaattt    9420
tgtttgttcc ctataccctac tccctaattc tttagttcct tcctgctcag gtcccttcat   9480
ttgtactttg gagtttttct catgtaaatt tgtataatgg aaaatattgt tcagtttgga    9540
tagaaagcat ggagaaataa ataaaaaaag atagctgaaa atcaaattga agaaatttat    9600
ttctgtgtaa agttatttaa aaactctgta ttatatttaa agaaaaaagc caacccccc     9660
aaaaagtgct atgtaattga tgtgaatatg cgaatactgc tataataaag attgactgca    9720
tggagaaa                                                            9728
```

<210> SEQ ID NO 5
<211> LENGTH: 22
<212> TYPE: DNA
<213> ORGANISM: Artificial Sequence
<220> FEATURE:
<223> OTHER INFORMATION: BRAF_LCM_F

```
<400> SEQUENCE: 5
tgcttgctct gataggaaaa tg                                              22

<210> SEQ ID NO 6
<211> LENGTH: 22
<212> TYPE: DNA
<213> ORGANISM: Artificial Sequence
<220> FEATURE:
<223> OTHER INFORMATION: BRAF_LCM_R

<400> SEQUENCE: 6
agcctcaatt cttaccatcc ac                                              22

<210> SEQ ID NO 7
<211> LENGTH: 19
<212> TYPE: DNA
<213> ORGANISM: Artificial Sequence
<220> FEATURE:
<223> OTHER INFORMATION: LSL-BrafV600E Fwd

<400> SEQUENCE: 7
cccaggctct ttatgagaa                                                  19

<210> SEQ ID NO 8
<211> LENGTH: 22
<212> TYPE: DNA
<213> ORGANISM: Artificial Sequence
<220> FEATURE:
<223> OTHER INFORMATION: LSL-BrafWT Rev

<400> SEQUENCE: 8
agtcaatcat ccacagagac ct                                              22

<210> SEQ ID NO 9
<211> LENGTH: 19
<212> TYPE: DNA
<213> ORGANISM: Artificial Sequence
<220> FEATURE:
<223> OTHER INFORMATION: LSL-BrafV600E Rev

<400> SEQUENCE: 9
gcttggctgg acgtaaacc                                                  19
```